US007888483B2

(12) United States Patent
Cohen et al.

(10) Patent No.: US 7,888,483 B2
(45) Date of Patent: Feb. 15, 2011

(54) ANTAGONISTS OF PROTEASE ACTIVATED RECEPTOR-1 (PAR1)

(75) Inventors: Steve B Cohen, San Diego, CA (US); Marc Nasoff, San Diego, CA (US)

(73) Assignee: IRM LLC, Hamilton (BM)

( * ) Notice: Subject to any disclaimer, the term of this patent is extended or adjusted under 35 U.S.C. 154(b) by 0 days.

(21) Appl. No.: 11/778,924

(22) Filed: Jul. 17, 2007

(65) Prior Publication Data

US 2008/0044424 A1   Feb. 21, 2008

Related U.S. Application Data

(60) Provisional application No. 60/831,800, filed on Jul. 18, 2006.

(51) Int. Cl.
*C07K 16/00* (2006.01)
*C07K 16/28* (2006.01)
*A61K 39/395* (2006.01)

(52) U.S. Cl. .............................. 530/388.22; 530/387.1; 530/387.3; 530/388.1; 424/130.1; 424/135.1; 424/141.1; 424/143.1

(58) Field of Classification Search ...................... None
See application file for complete search history.

(56) References Cited

U.S. PATENT DOCUMENTS 5,840,499 A * 11/1998 Brass et al. ................. 435/7.1
2006/0216290 A1* 9/2006 Golz et al. ............... 424/144.1

FOREIGN PATENT DOCUMENTS

WO   WO01007072   2/2001
WO   WO2008011107   1/2008

OTHER PUBLICATIONS

Rudikoff et al. PMAS 1982 79:1979.*
Brass et al. JBC 1992, 267:13795-13798.*
Batori et al. Protein Engineering 2002, 15:1015-1020.*
Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Darmoul et al, "Activation of Proteinase-Activated Receptor 1 Promotes Human Colon Cancer Cell Proliferation Through Epidermal Growth Factor Receptor Transactivation," Sep. 2004, 2, 514-522.
Junge et al., "The contribution of protease-activated receptor 1 to neuronal damage caused by transient focal cerebral ischemia," 2003, Proc. Natl. Acad. Sci., U.S.A., 100(22), 13019-13024.
Rondeau et al., "Role of Thrombin Receptors in the Kidney: Lessons from PAR1 Knock-Out Mice," 2001, Nephrol. Dial. transplant, vol. 16, pp. 1529-1531.

Salah et al., "Protease-Activated Receptor-1 (*hPar1*), A Survival Factor Eliciting Tumor Progression," 2007, Mol. Cancer, Mar. 2007, 5, 229-240.
Santos et al., "Interaction of Viper Venom Serine Peptidase with Thrombin Receptors on Human Platelets," 2000, FEBS Letters, vol. 477, pp. 199-202.
Sevastos et al., "Tissue Factor Deficiency and PAR-1 Deficiency are Protective Against Renel Ischemia repurfusion Injury," 2007, Blood, 109(2), 577-583.
Tsuboi et al, "Role of the thrombin/protease-activated receptor 1 pathway in intestinal ischemia-reperfusion injury in rats," 2007, Am. J. Physiol. Gastrointest. Liver. Physiol., 292, G678-683.
Vegnole et al., "A role for proteinase-activated receptor-1 in inflammatory bowel diseases," 2004, J. Clin. Invest., 114, 10, 1444.
Ahn et al., Inhibition of Cellular Action of Thrombin by N3-Cyclopropyl-7-{[4-(1-Methylethyl)Phenyl]Methyl}-7H-Pyrrolo [3,2-f]Quinazoline-1,3-Diamine (SCH 79797), a Nonpeptide Thrombin Receptor Antagonist; Biochemical Pharmacology, Apr. 2000, pp. 1425-1434, vol. 60, Elsevier.
Ahn et al., Structure-Activity Relationships of Pyrroloquinazolines as Thrombin Receptor Antagonists; Bioorganic & Medicinal Chemistry Letters, Jun. 8, 1999, pp. 2073-2078, vol. 9, Elsevier.
Albrektsen et al., Transcriptional Program Induced by Factor VIIa-Tissue Factor, PAR1 and PAR2 in MDA-MB-231 Cells; J Thromb Haemost, 2007, pp. 1588-1597, vol. 5, Wiley-Blackwell, US.
Bernatowicz et al., Development of Potent Thrombin Receptor Antagonist Peptides, J. Med. Chem., 1996, pp. 4879-4887, vol. 39, No. 25, ACS Publications, US.
Boire et al., PAR1 is a Matrix Metalloprotease-1 Receptor that Promotes Invasion and Tumorigenesis of Breast Cancer Cells; Cell, Feb. 11, 2005, pp. 303-313, vol. 120, Elsevier.
Buresi et al., Activation of Proteinase-Activated Receptor-1 Inhibits Neurally Evoked Chloride Secretion in the Mouse Colon in Vitro; AJP Gastrointest Liver Physiol, Sep. 2, 2004, pp. G337-G345, vol. 288, American Physiological Society, US.
Camerer et al., Platelets, Protease-Activated Receptors, and Fibrinogen in Hematogenous Metastasis; Blood, Mar. 18, 2004, pp. 397-401, vol. 104, No. 2, The American Society of Hematology, US.
Cenac et al., Proteinase-Activated Receptor-1 is an Anti-Inflammatory Signal for Colitis Mediated by a Type 2 Immune Response; Inflamm Bowel Dis, Sep. 2005, pp. 792-798, vol. 11, No. 9, Lippincott Williams & Wilkins, US.
Chambers et al., Thrombin is a Potent Inducer of Connective Tissue Growth Factor Production via Proteolytic Activation of Protease-activated Receptor-1, The Journal of Biological Chemistry, Nov. 10, 2000, pp. 35584-35591, vol. 275, No. 4, The American Society for Biochemistry and Molecular Biology, US.

(Continued)

*Primary Examiner*—Sharon Wen
(74) *Attorney, Agent, or Firm*—Kilpatrick Townsend & Stockton LLP

(57) ABSTRACT

The present invention provides antibodies or antigen-binding molecules that specifically recognize and antagonize human PAR1 receptor. Also provided in the invention are polynucleotides and vectors that encode such molecules and host cells that harbor the polynucleotides or vectors.

22 Claims, 5 Drawing Sheets

OTHER PUBLICATIONS

Di Paola et al., Beneficial Effects of GW274150 Treatment on the Development of Experimental Colitis Induced by Dinitrobenzene Sulfonic Acid; European Journal of Pharmacology, Dec. 31, 2004, pp. 281-289, vol. 507, Elsevier.

Dixit et al., Nitric oxide Mediates Increased P-Glycoprotein Activity in Interferon-g-Stimulated Human Intestinal Cells; AJP Gastrointest Liver Physiol, Oct. 14, 2004, pp. G533-540, vol. 288, American Physiological Society, US.

Domotor et al., Activated protein C alters cytosolic calcium flux in human brain endothelium via binding to endothelial protein C receptor and activation of protease activated receptor-1, Blood, Jun. 15, 2003, pp. 4797-4801, vol. 101, No. 12, The American Society of Hematology, US.

Gudmundsdottir et al., Direct Vascular Effects of Protease-Activated Receptor Type 1 Agonism in Vivo in Humans; Circulation, Oct. 10, 2006, pp. 1625-1632, American Heart Association, US.

Hollenberg et al., Proteinase-Activated Receptors; Pharmacological Reviews, 2002, pp. 203-217, vol. 54, No. 2, the American Society for Pharmacology and Experimental Therapeutics, US.

Hu et al., Role of Endogenous in Thrombin in Tumor Implantation, Seeding and Spontaneous Metastasis; Blood First Edition Paper, Jul. 20, 2004, pp. 2746-2751, The American Society of Hematology, US.

Kahn et al., Protease-activated receptors 1 and 4 mediate activation of human platelets by thrombin, The Journal of Clinical Investigation, Mar., 1999, pp. 879-888, vol. 103, No. 6, American Society for Clinical Investigation, US.

Kriegelstein et al., Regulation of Murine Intestinal Inflammation by Reactive Metabolites of Oxygen and Nitrogen; Divergent Roles of Superoxide and Nitric Oxide; J. Exp. Med., Oct. 29, 2001, pp. 1207-1218, vol. 194, No. 9, The Rockefeller University Press, US.

Massi et al., Expression of protease-activated receptors 1 and 2 in melanocytic nevi and malignant melanomia, Human Pathology, 2005, vol. 36, pp. 676-685, Elsevier.

McCafferty et al., Role of Inducible Nitric Oxide synthase in Trinitrobenzene Sulphonic Acid Induced Colitis in Mice; GUT online, 1999, pp. 864-873, vol. 45, BMJ Group, London.

McLaughlin et al., Functional Selectivity of G Protein Signaling by Agonist Peptides and Thrombin for the Protease-Activated Receptor-1; The Journal of Biological Chemistry, Jul. 1, 2005, pp. 25048-25059, vol. 280, No. 26, The American Society for Biochemistry and Molecular Biology, Inc., US.

Molino et al., Thrombin Receptors on Human Platelets, The Journal of Biological Chemistry, Feb. 27, 1997, pp. 6011-6017, vol. 272, No. 9, The American Society for Biochemistry and Molecular Biology, Inc., US.

Rasmussen et al., cDNA cloning and expression of a hamster alpha-thrombin receptor coupled to Ca2+ mobilization, Federation of European Biochemical Societies, Aug. 1991, pp. 123-128, vol. 288, No. 1,2, Elsevier.

Strande et al., SCH 79797, a Selective PAR1 Antagonist, Limits Myocardial Ischemia/Reperfusion Injury in Rat Hearts; Basic Research in Cardiology, Apr. 30, 2007, pp. 350-358, vol. 102, No. 4, Steinkopff Verlag, Germany.

Vassallo et al., Structure-Function Relationships in the Activation of Platelet Thrombin Receptors by Receptor-derived Peptides, The Jornal of Biological Chemistry, Mar. 25, 1992, pp. 6081-6085, vol. 267, No. 9, The American Society for Biochemistry and Molecular Biology, US.

Vergnolle et al., A Role for Proteinase-Activated Receptor-1 in Inflammatory Bowel Diseases; The Journal of Clinical Investigation, Nov. 2004, pp. 1444-1456, vol. 114, No. 10, American Society for Clinical Investigation, US.

Zingarelli et al., Reduced Oxidative and Nitrosative Damage in Murine Experimental Colitis in the Absence of Inducible Nitric Oxide Synthase; GUT Online, 1999, pp. 199-209, vol. 45, BMJ Group, London.

* cited by examiner

*Figure 1*

Clone 4E7.J14.L16 – heavy chain (SEQ ID NO:1)
GAGGTCCAGCTGCAACAGTCTGGACCTGTGCTGGTGAAGCCTGGGGCTTCAGTGAAGATGTCCTGTGAGGCTTCTGGATACACATTCA
CTGACTACTATATGAACTGGGTGAAGCAGAGCCATGGAAAGAGCCTTGAGTGGATTGGAGTTATTGATCCTTACAACGGCCGTTCTAG
GTACAACCAGATGTTCAAGGGCAAGGCCACAATGACTGTTGACAAGTCCTCCAGCACAGCCTACATGGAGCTCAACAACCTGACATCT
AAGACTCTGCAGTCTATTACTGTGCAAGCGATGATGGTCCATCCACTGTACTTCGATGTCTGGGGCACAGGGACCACGGTCACCG
TCTCCTCA

Clone 4E7.J14.L16 – light chain (SEQ ID NO:2)
GATGTTTTGATGACCCAAACTCCACTCTCCCTGCCTGTCAGTCTTGGAGATCAAGCCTCCATCTCTTGCAGATCTAGTCAGAACATTG
TACATAGTAATGGAAACACCTATTTAGAATGGTACCTGCAGAAATGGTACCTGCAGAAACCAGGCCAGTCTCCAAAGCTCCTGATCTACAAAGTTTCCAACCG
ATTTTCTGGGGTCCCAGACAGGTTCAGTGGCAGTGGATCAGGGACAGATTTCACACTCAAGATCAGCAGAGTGGAGGCTGAGGATCTG
GGAATTTATTACTGTTTTCAAGGTTCACATGTTCCATTCACGTTCGGCTCGGGGACAAAGTTGGAAATAAAA

Clone 6E11.H6.A9 – heavy chain (SEQ ID NO:3)
CAGGTTCAGCTGCAACAGTCTGGACCTGAGCTGGTGGTGAGCTTCAGTGAAGATATCCTGCAAGGTTTCTGGCTACACCTTCA
CTGACCATACTTTCACTGGATGAATCAGAGGCCTGACAGGCCTGGAATGGATTGGATATATTTTCCTAGAGATGGTAGTACTAA
GTACAATGAGAAGTTCAAGGGCAAGGCCACATTGACTGCAGACAAATCCTCCAGCACAGCCTACATGCAGCTCAGCAGCCTAACGTCT
GTGACTCTGCAGTCTATTTCTGTGCAAGCCATTACTACGGTAGTTTTGAGTACTGGGGCCAAGGCACCACTCTCACAGTCGCCTC

Clone 6E11.H6.A9 – light chain (SEQ ID NO:4)
GATGTTGTGATGACCCAAACTCCACTCTCCCTGCCTGTCAGTCTTGGAGATCAAGCCTCCATCTCTTGCAGATCTAGTCAGAGCCTTG
TACACAGTAATGGAAACACCTATTTACATTGGTACCTGCAGAAGCCAGGCCAGTCTCCAAAGCTCCTGATCTACAAAGTTTCCAACCG
ATTTTCTGGGGTCCCAGACAGGTTCAGTGGCAGTGGATCAGGGACAGATTTCACACTCAAGATCAGCAGAGTGGAGGCTGAGGATCTG
GGAGTTTATTTCTGCTCTCAAAGTACACACATCTTCCGCTCACGTTCGGTGCTGGGACCAAGCTGGAGCTGAAA

*Figure 2*

Clone 4E7.J14.L16 - heavy chain (SEQ ID NO:5)
EVQLQQSGPVLVKPGASVKMSCEASGYTFTDYMNWVKQSHGKSLEWIGVIDPHNGRSRYN
QMFKGKATMTVDKSSSTAYMELNNLTSKDSAVYYCASDDGPSHWYFDVWGTGTTVTVSS

Clone 4E7.J14.L16 - light chain (SEQ ID NO:6)
DVLMTQTPLSLPVSLGDQASISCRSSQNIVHSNGNTYLEWYLQTPGQSPKLLIYKVSNRFS
GVPDRFSGSGSGTDFTLKISRVEAEDLGIYYCFQGSHVPFTFGSGTKLEIK

Clone 6E11.H6.A9 - heavy chain (SEQ ID NO:7)
QVQLQQSDAELVKPGASVKISCKVSGYTFTDHTFHWMNQRPGQGLEWIGYIFPRDGSTKYN
EKFKGKATLTADKSSSTAYMQLSSLTSVDSAVYFCASHYYGSFEYWGQGTTLTVA

Clone 6E11.H6.A9- light chain (SEQ ID NO:8)
DVVMTQTPLSLPVSLGDQASISCRSSQSLVHSNGNTYLHWYLQKPGQSPKLLIYKVSNRFS
GVPDRFSGSGSGTDFTLKISRVEAEDLGVYFCSQSTHLPLTFGAGTKLELK

SEQUENCE LISTING

```
<160> NUMBER OF SEQ ID NOS: 38

<210> SEQ ID NO 1
<211> LENGTH: 360
<212> TYPE: DNA
<213> ORGANISM: Mus musculus
<220> FEATURE:
<223> OTHER INFORMATION: clone 4E7.J14.L16 anti-human protease activated
      receptor-1 (PAR1) antibody heavy chain variable
      region

<400> SEQUENCE: 1
gaggtccagc tgcaacagtc tggacctgtg ctggtgaagc ctggggcttc agtgaagatg      60
tcctgtgagg cttctggata cacattcact gactactata tgaactgggt gaagcagagc     120
catggaaaga gccttgagtg gattggagtt attgatcctc acaacggccg ttctaggtac     180
aaccagatgt tcaagggcaa ggccacaatg actgttgaca agtcctccag cacagcctac     240
atggagctca caacctgac atctaaagac tctgcagtct attactgtgc aagcgatgat      300
ggtccatccc actggtactt cgatgtctgg ggcacaggga ccacggtcac cgtctcctca     360

<210> SEQ ID NO 2
<211> LENGTH: 336
<212> TYPE: DNA
<213> ORGANISM: Mus musculus
<220> FEATURE:
<223> OTHER INFORMATION: clone 4E7.J14.L16 anti-human protease activated
      receptor-1 (PAR1) antibody light chain variable
      region

<400> SEQUENCE: 2
gatgttttga tgacccaaac tccactctcc ctgcctgtca gtcttggaga tcaagcctcc      60
atctcttgca gatctagtca gaacattgta catagtaatg gaaacaccta tttagaatgg     120
tacctgcaga caccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggaatt tattactgtt ttcaaggttc acatgttcca     300
ttcacgttcg gctcggggac aaagttggaa ataaaa                              336

<210> SEQ ID NO 3
<211> LENGTH: 350
<212> TYPE: DNA
<213> ORGANISM: Mus musculus
<220> FEATURE:
<223> OTHER INFORMATION: clone 6E11.H6.A9 anti-human protease activated
      receptor-1 (PAR1) antibody heavy chain variable
      region
```

<400> SEQUENCE: 3

```
caggttcagc tgcaacagtc tgacgctgag ttggtgaaac ctggagcttc agtgaagata      60
tcctgcaagg tttctggcta caccttcact gaccatactt ttcactggat gaatcagagg    120
cctggacagg gcctggaatg gattggatat attttttccta gagatggtag tactaagtac    180
aatgagaagt tcaagggcaa ggccacattg actgcagaca atcctccag cacagcctac     240
atgcagctca gcagcctaac gtctgtggac tctgcagtct atttctgtgc aagccattac    300
tacggtagtt ttgagtactg gggccaaggc accactctca cagtcgcctc                350
```

<210> SEQ ID NO 4
<211> LENGTH: 336
<212> TYPE: DNA
<213> ORGANISM: Mus musculus
<220> FEATURE:
<223> OTHER INFORMATION: clone 6E11.H6.A9 anti-human protease activated
     receptor-1 (PAR1) antibody light chain variable
     region

<400> SEQUENCE: 4

```
gatgttgtga tgacccaaac tccactctcc ctgcctgtca gtcttggaga tcaagcctcc      60
atctcttgca gatctagtca gagccttgta cacagtaatg aaacaccta tttacattgg    120
tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatcttccg    300
ctcacgttcg gtgctgggac caagctggag ctgaaa                              336
```

<210> SEQ ID NO 5
<211> LENGTH: 120
<212> TYPE: PRT
<213> ORGANISM: Mus musculus
<220> FEATURE:
<223> OTHER INFORMATION: clone 4E7.J14.L16 anti-human protease activated
     receptor-1 (PAR1) antibody heavy chain variable
     region

<400> SEQUENCE: 5

```
Glu Val Gln Leu Gln Gln Ser Gly Pro Val Leu Val Lys Pro Gly Ala
 1               5                  10                  15

Ser Val Lys Met Ser Cys Glu Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asp Pro His Asn Gly Arg Ser Arg Tyr Asn Gln Met Phe
    50                  55                  60

Lys Gly Lys Ala Thr Met Thr Val Asp Lys Ser Ser Ser Thr Ala Tyr
65                  70                  75                  80

Met Glu Leu Asn Asn Leu Thr Ser Lys Asp Ser Ala Val Tyr Tyr Cys
                85                  90                  95

Ala Ser Asp Asp Gly Pro Ser His Trp Tyr Phe Asp Val Trp Gly Thr
            100                 105                 110

Gly Thr Thr Val Thr Val Ser Ser
        115                 120
```

<210> SEQ ID NO 6
<211> LENGTH: 112
<212> TYPE: PRT
<213> ORGANISM: Mus musculus

```
<220> FEATURE:
<223> OTHER INFORMATION: clone 4E7.J14.L16 anti-human protease activated
      receptor-1 (PAR1) antibody light chain variable
      region

<400> SEQUENCE: 6

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Asn Ile Val His Ser
            20                  25                  30

Asn Gly Asn Thr Tyr Leu Glu Trp Tyr Leu Gln Thr Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 7
<211> LENGTH: 116
<212> TYPE: PRT
<213> ORGANISM: Mus musculus
<220> FEATURE:
<223> OTHER INFORMATION: clone 6E11.H6.A9 anti-human protease activated
      receptor-1 (PAR1) antibody heavy chain variable
      region

<400> SEQUENCE: 7

Gln Val Gln Leu Gln Gln Ser Asp Ala Glu Leu Val Lys Pro Gly Ala
 1               5                  10                  15

Ser Val Lys Ile Ser Cys Lys Val Ser Gly Tyr Thr Phe Thr Asp His
            20                  25                  30

Thr Phe His Trp Met Asn Gln Arg Pro Gly Gln Gly Leu Glu Trp Ile
        35                  40                  45

Gly Tyr Ile Phe Pro Arg Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Ser His Tyr Tyr Gly Ser Phe Glu Tyr Trp Gly Gln Gly Thr Thr
            100                 105                 110

Leu Thr Val Ala
        115

<210> SEQ ID NO 8
<211> LENGTH: 112
<212> TYPE: PRT
<213> ORGANISM: Mus musculus
<220> FEATURE:
<223> OTHER INFORMATION: clone 6E11.H6.A9 anti-human protease activated
      receptor-1 (PAR1) antibody light chain variable
      region

<400> SEQUENCE: 8

Asp Val Val Met Thr Gln Thr Pro Leu Ser Leu Pro Val Ser Leu Gly
 1               5                  10                  15
```

```
Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Leu Pro Leu Thr Phe Gly Ala Gly Thr Lys Leu Glu Leu Lys
            100                 105                 110
```

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 1 (CDR1)

<400> SEQUENCE: 9
gactactata tgaac                                                      15

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 2 (CDR2)

<400> SEQUENCE: 10
gttattgatc ctcacaacgg ccgttctagg tacaaccaga tgttcaaggg c               51

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 3 (CDR3)

<400> SEQUENCE: 11
gatgatggtc catcccactg gtacttcgat gtc                                  33

<210> SEQ ID NO 12
<211> LENGTH: 48
<212> TYPE: DNA
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody light chain variable
      region complementarity determining region 1 (CDR1)

<400> SEQUENCE: 12
agatctagtc agaacattgt acatagtaat ggaaacacct atttagaa                  48

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:clone
    4E7.J14.L16 anti-human protease activated
    receptor-1 (PAR1) antibody light chain variable
    region complementarity determining region 2 (CDR2)

<400> SEQUENCE: 13
aaagtttcca accgattttc t                                              21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:clone
    4E7.J14.L16 anti-human protease activated
    receptor-1 (PAR1) antibody light chain variable
    region complementarity determining region 3 (CDR3)

<400> SEQUENCE: 14
tttcaaggtt cacatgttcc attcacg                                        27

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:clone
    6E11.H6.A9 anti-human protease activated
    receptor-1 (PAR1) antibody heavy chain variable
    region complementarity determining region 1 (CDR1)

<400> SEQUENCE: 15
gaccatactt ttcac                                                     15

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence:clone
    6E11.H6.A9 anti-human protease activated
    receptor-1 (PAR1) antibody heavy chain variable
    region complementarity determining region 2 (CDR2)

<400> SEQUENCE: 16 tatattttc ctagagatgg tagtactaag tacaatgaga agttcaaggg c               51

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:clone
    6E11.H6.A9 anti-human protease activated
    receptor-1 (PAR1) antibody heavy chain variable
    region complementarity determining region 3 (CDR3)

<400> SEQUENCE: 17
cattactacg gtagttttga gtac                                            24

<210> SEQ ID NO 18
<211> LENGTH: 48
<212> TYPE: DNA
<213> ORGANISM: Artificial Sequence
<220> FEATURE:
<223> OTHER INFORMATION: Description of Artificial Sequence:clone
      6E11.H6.A9 anti-human protease activated
      receptor-1 (PAR1) antibody light chain variable
      region complementarity determining region 1 (CDR1)

<400> SEQUENCE: 18
agatctagtc agagccttgt acacagtaat ggaaacacct atttacat                48

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:clone
      6E11.H6.A9 anti-human protease activated
      receptor-1 (PAR1) antibody light chain variable
      region complementarity determining region 2 (CDR2)

<400> SEQUENCE: 19
aaagtttcca accgattttc t                                             21

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:clone
      6E11.H6.A9 anti-human protease activated
      receptor-1 (PAR1) antibody light chain variable
      region complementarity determining region 3 (CDR3)

<400> SEQUENCE: 20
tctcaaagta cacatcttcc gctcacg                                       27

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 1 (CDR1)

<400> SEQUENCE: 21

Asp Tyr Tyr Met Asn
 1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 2 (CDR2)

<400> SEQUENCE: 22

Val Ile Asp Pro His Asn Gly Arg Ser Arg Tyr Asn Gln Met Phe Lys
 1               5                  10                  15
Gly

<210> SEQ ID NO 23
<211> LENGTH: 11
<212> TYPE: PRT
<213> ORGANISM: Artificial Sequence -continued

```
<220> FEATURE:
<223> OTHER INFORMATION: Description of Artificial Sequence:clone
      4E7.J14.L16 anti-human protease activated
      receptor-1 (PAR1) antibody heavy chain variable
      region complementarity determining region 3 (CDR3)

<400> SEQUENCE: 23

Asp Asp Gly Pro Ser His Trp Tyr Phe Asp Val
  1               5                  10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody light chain variable
      region complementarity determining region 1 (CDR1)

<400> SEQUENCE: 24

Arg Ser Ser Gln Asn Ile Val His Ser Asn Gly Asn Thr Tyr Leu Glu
  1               5                  10                  15

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody light chain variable
      region complementarity determining region 2 (CDR2)

<400> SEQUENCE: 25

Lys Val Ser Asn Arg Phe Ser
  1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:clone
      4E7.J14.L16 anti-human protease activated
      receptor-1 (PAR1) antibody light chain variable
      region complementarity determining region 3 (CDR3)

<400> SEQUENCE: 26

Phe Gln Gly Ser His Val Pro Phe Thr
  1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:clone
      6E11.H6.A9 anti-human protease activated
      receptor-1 (PAR1) antibody heavy chain variable
      region complementarity determining region 1 (CDR1)

<400> SEQUENCE: 27

Asp His Thr Phe His
  1               5

<210> SEQ ID NO 28
<211> LENGTH: 17
<212> TYPE: PRT
```

<213> ORGANISM: Artificial Sequence
<220> FEATURE:
<223> OTHER INFORMATION: Description of Artificial Sequence:clone
6E11.H6.A9 anti-human protease activated
receptor-1 (PAR1) antibody heavy chain variable
region complementarity determining region 2 (CDR2)

<400> SEQUENCE: 28

Tyr Ile Phe Pro Arg Asp Gly Ser Thr Lys Tyr Asn Glu Lys Phe Lys
 1               5                   10                  15

Gly

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:clone
6E11.H6.A9 anti-human protease activated
receptor-1 (PAR1) antibody heavy chain variable
region complementarity determining region 3 (CDR3)

<400> SEQUENCE: 29

His Tyr Tyr Gly Ser Phe Glu Tyr
 1               5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence:clone
6E11.H6.A9 anti-human protease activated
receptor-1 (PAR1) antibody light chain variable
region complementarity determining region 1 (CDR1)

<400> SEQUENCE: 30

Arg Ser Ser Gln Ser Leu Val His Ser Asn Gly Asn Thr Tyr Leu His
 1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:clone
6E11.H6.A9 anti-human protease activated
receptor-1 (PAR1) antibody light chain variable
region complementarity determining region 2 (CDR2)

<400> SEQUENCE: 31

Lys Val Ser Asn Arg Phe Ser
 1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:clone
6E11.H6.A9 anti-human protease activated
receptor-1 (PAR1) antibody light chain variable
region complementarity determining region 3 (CDR3)

<400> SEQUENCE: 32

Ser Gln Ser Thr His Leu Pro Leu Thr
 1               5

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence:RT-PCR heavy
      chain variable region (VH) primer HV1

<400> SEQUENCE: 33
gggtctagac accatggrat gsagctgkgt matsctctt                          39

<210> SEQ ID NO 34
<211> LENGTH: 39
<212> TYPE: DNA
<213> ORGANISM: Artificial Sequence
<220> FEATURE:
<223> OTHER INFORMATION: Description of Artificial Sequence:RT-PCR heavy
      chain constant region primer H-Constant

<400> SEQUENCE: 34
gcgtctagaa yctccacaca caggrrccag tggatagac                          39

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence:RT-PCR light
      chain variable region (VL) primer LV5
<220> FEATURE:
<221> NAME/KEY: modified_base
<222> LOCATION: (39)
<223> OTHER INFORMATION: n = g, a, c or t

<400> SEQUENCE: 35
gggtctagac accatgaagt tgcctgttag gctgttgdna                         40

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence:RT-PCR light
      chain constant region primer L-Constant

<400> SEQUENCE: 36
gcgtctagaa ctggatggtg ggaagatgg                                     29

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence:new PAR1
      N-terminus after proteolytic removal of portion of
      extracellular N-terminal domain

<400> SEQUENCE: 37

Ser Phe Leu Leu Arg Asn
 1               5

<210> SEQ ID NO 38
<211> LENGTH: 27
<212> TYPE: PRT
<213> ORGANISM: Artificial Sequence
<220> FEATURE:
<223> OTHER INFORMATION: Description of Artificial Sequence:anti-PAR1
      antibody or antigen-binding molecule epitope
      within PAR1 N-terminal tethered ligand

```
<400> SEQUENCE: 38

Ser Phe Leu Leu Arg Asn Pro Asn Asp Lys Tyr Glu Pro Phe Trp Glu
 1               5                  10                      15

Asp Glu Glu Lys Asn Glu Ser Gly Leu Thr Glu
                20                  25
```

ANTAGONISTS OF PROTEASE ACTIVATED RECEPTOR-1 (PAR1)

CROSS-REFERENCES TO RELATED APPLICATIONS

This application claims the benefit of U.S. Provisional Application No. 60/831,800, filed on Jul. 18, 2006, the entire disclosure of which is hereby incorporated herein by reference for all purposes.

FIELD OF THE INVENTION

The present invention relates to antibody and antigen binding molecule antagonists of protease activated receptor-1 (PAR1).

BACKGROUND OF THE INVENTION

The protease-activated receptor 1 (PAR1) is a thrombin receptor which belongs to the class of G protein-coupled receptors (GCPR). PAR1 is expressed in various tissues, e.g., endothelial cells, smooth muscles cells, fibroblasts, neurons and human platelets. It is involved in cellular responses associated with hemostasis, proliferation, and tissue injury. Thrombin-mediated stimulation of platelet aggregation via PAR1 is an important step in clot formation and wound healing in blood vessels. Thrombin activates PAR1 by proteolytic removal of a portion of the extracellular N-terminal domain of PAR1 and exposing a new PAR1 N-terminus. The first few amino acids (SFLLRN; SEQ ID NO:37) of the new PAR1 N-terminus then act as a tethered ligand that binds to another part of the receptor to initiate signaling by an associated G-protein. PAR1 can also be activated by other serine proteases involved in blood clotting.

Modulation of PAR1-mediated signaling activities has several therapeutic applications. Inhibition of PAR1 is helpful for treating thrombotic and vascular proliferative disorders as well as for inhibiting progression of cancers. See, for example, Darmoul, et al., *Mol Cancer Res* (2004) 2(9):514-22 and Salah, et al, *Mol Cancer Res* (2007) 5(3):229-40. A PAR1 inhibitor, including an antagonist antibody or antigen binding molecule, has utility in the treatment of numerous disease conditions mediated by PAR1 intracellular signaling. For example, a PAR1 inhibitor, including an antagonist antibody or antigen binding molecule, finds use in preventing or inhibiting chronic intestinal inflammatory disorders, including inflammatory bowel disease (IBD), irritable bowel syndrome (IBS) and ulcerative colitis; and fibrotic disorders, including liver fibrosis and lung fibrosis. See, for example, Vergnolle, et al., *J Clin Invest* (2004) 114(10): 1444; Yoshida, et al, *Aliment Pharmacol Ther* (2006) 24(Suppl 4):249; Mercer, et al., *Ann NY Acad Sci* (2007) 1096:86-88; Sokolova and Reiser, *Pharmacol Ther* (2007) PMID: 17532472. A PAR1 inhibitor, including an antagonist antibody or antigen binding molecule, also finds use in preventing or inhibiting ischemia-reperfusion injury, including myocardial, renal, cerebral and intestinal ischemia-reperfusion injury. See, for example, Strande, et al., *Basic Res. Cardiol* (2007) 102(4):350-8; Sevastos, et al., *Blood* (2007) 109(2):577-583; Junge, et al., *Proc Natl Acad Sci USA*. (2003) 100(22):13019-24 and Tsuboi, et al., *Am J Physiol Gastrointest Liver Physiol* (2007) 292(2): G678-83. Inhibiting PAR1 intracellular signaling can also be used to inhibit herpes simple virus (HSV1 and HSV2) infection of cells. See, Sutherland, et al., *J Thromb Haemost* (2007) 5(5):1055-61.

BRIEF SUMMARY OF THE INVENTION

In one aspect, the present invention provides monoclonal antagonist antibodies or antigen-binding molecules against human protease activated receptor-1 (hPAR1). The antibodies or antigen-binding molecules bind to human PAR1 with the same binding specificity as that of a second antibody. The second antibody has (i) a heavy chain variable region sequence of SEQ ID NO:5 and a light chain variable region sequence of SEQ ID NO:6 or (ii) a heavy chain variable region sequence of SEQ ID NO:7 and a light chain variable region sequence of SEQ ID NO:8.

In some embodiments, the antibodies specifically bind to an epitope of hPAR1 comprising the amino acid sequence SFLLRNPNDKYEPFWEDEEKNESGLTE (SEQ ID NO:38), or fragments thereof, for example, a fragment of at least 8, 9, 10, 11, 12, 13, 14 or 15 contiguous amino acids. In some embodiments, the antibodies do not significantly bind to (i.e., cross-react with) PAR1 from another species (e.g., mouse PAR1 (mPAR1)) or a PAR subtype other than PAR1, for example, protease activated receptor-2 (PAR2).

Some of the antibodies or antigen-binding molecules have a heavy chain complementarity determining region (CDR) sequence of SEQ ID NO:21, SEQ ID NO:22 or SEQ ID NO:23; or a light chain CDR sequence of SEQ ID NO:24, SEQ ID NO:25, or SEQ ID NO:26. Some of these molecules have heavy chain CDR1, CDR2, and CDR3 sequences, SEQ ID NO:21, SEQ ID NO:22 and SEQ ID NO:23, respectively; and light chain CDR1, CDR2, and CDR3 sequences, SEQ ID NO:24, SEQ ID NO:25, and SEQ ID NO:26, respectively.

Some of the antibodies or antigen-binding molecules have a heavy chain complementarity determining region (CDR) sequence of SEQ ID NO:27, SEQ ID NO:28 or SEQ ID NO:29; or a light chain CDR sequence of SEQ ID NO:30, SEQ ID NO:31, or SEQ ID NO:32. Some of these molecules have heavy chain CDR1, CDR2, and CDR3 sequences, SEQ ID NO:27, SEQ ID NO:28 and SEQ ID NO:29, respectively; and light chain CDR1, CDR2, and CDR3 sequences, SEQ ID NO:30, SEQ ID NO:31, and SEQ ID NO:32, respectively.

Some of the antibodies or antigen-binding molecules have a heavy chain variable region amino acid sequence that is at least 85%, 90%, 95%, 96, 97%, 98%, 99% or 100% identical to SEQ ID NO:5 and a light chain variable region amino acid sequence that is at least 85%, 90%, 95%, 96, 97%, 98%, 99% or 100% identical to SEQ ID NO:6. Some others have a heavy chain variable region amino acid sequence that is at least 85%, 90%, 95%, 96, 97%, 98%, 99% or 100% identical to SEQ ID NO:7 and a light chain variable region amino acid sequence that is at least 85%, 90%, 95%, 96, 97%, 98%, 99% or 100% identical to SEQ ID NO:8. Some of the molecules have a heavy chain variable region amino acid sequence of SEQ ID NO:5 and a light chain variable region amino acid sequence of SEQ ID NO:6. Some others have a heavy chain variable region amino acid sequence of SEQ ID NO:7 and a light chain variable region amino acid sequence of SEQ ID NO:8.

Some of the antibodies or antigen-binding molecules have a heavy chain variable region amino acid sequence that is at least 85%, 90%, 95%, 96, 97%, 98%, 99% or 100% identical to SEQ ID NO:5 or SEQ ID NO:7. Some of the antibodies or antigen-binding molecules have a light chain variable region amino acid sequence that is at least 85%, 90%, 95%, 96, 97%, 98%, 99% or 100% identical to SEQ ID NO:6 or SEQ ID NO:8.

Some of the anti-hPAR1 antibodies or antigen-binding molecules of the invention are mouse antibodies. Some others are chimeric antibodies. Some of the anti-hPAR1 molecules are humanized antibodies. Some others are human antibodies. Still some others are single chain antibodies, Fab fragments, or monobodies with a scaffold derived from a human fibronectin type III domain.

In another aspect, the invention provides isolated or recombinant polynucleotides which encode a polypeptide containing the variable region of the heavy chain or the variable region of the light chain of the anti-hPAR1 antibody or antigen-binding molecules. Some of polynucleotides encode a polypeptide containing the variable region of a human antibody. The polypeptide can contain heavy chain CDR1, CDR2, and CDR3 sequences, SEQ ID NO:21, SEQ ID NO:22 and SEQ ID NO:23, respectively; and light chain CDR1, CDR2, and CDR3 sequences, SEQ ID NO:24, SEQ ID NO:25, and SEQ ID NO:26, respectively. The polypeptide can also contain heavy chain CDR1, CDR2, and CDR3 sequences, SEQ ID NO:27, SEQ ID NO:28 and SEQ ID NO:29, respectively; and light chain CDR1, CDR2, and CDR3 sequences, SEQ ID NO:30, SEQ ID NO:31, and SEQ ID NO:32, respectively.

Some of the polynucleotides encode a mature heavy chain variable region sequence that is at least 90% identical to the mature region of SEQ ID NO:5, and/or a mature light chain variable region sequence that is at least 90% identical to the mature region of SEQ ID NO:6. Some others encode a mature heavy chain variable region amino acid sequence that is at least 90% identical to SEQ ID NO:7 and/or a mature light chain variable region amino acid sequence that is at least 90% identical to SEQ ID NO:8. Some of the polynucleotides encode a mature heavy chain variable region sequence that is identical to the mature region of SEQ ID NO:5 and/or a mature light chain variable region sequence that is identical to the mature region of SEQ ID NO:6. Some other encode a mature heavy chain variable region sequence that is identical to the mature region of SEQ ID NO:7 and/or a mature light chain variable region sequence that is identical to the mature region of SEQ ID NO:8.

In another aspect, the invention provides isolated host cells which harbor (1) a recombinant DNA segment encoding a heavy chain of the anti-PAR1 antibody or antigen-binding molecule of the invention; and (2) a second recombinant DNA segment encoding a light chain of the antibody or antigen-binding molecule. In some of the host cells, the DNA segments are each operably linked to a promoter and are capable of being expressed in the host cells. Some of the host cells can express an anti-PAR1 antibody or antigen-binding molecule of human origin. Some of the host cells can express an anti-hPAR1 antibody or antigen-binding molecule that contains heavy chain CDR1, CDR2, and CDR3 sequences, SEQ ID NO:21, SEQ ID NO:22 and SEQ ID NO:23, respectively; and light chain CDR1, CDR2, and CDR3 sequences, SEQ ID NO:24, SEQ ID NO:25, and SEQ ID NO:26, respectively. Some others express an anti-hPAR1 antibody or antigen-binding molecule that contains heavy chain CDR1, CDR2, and CDR3 sequences, SEQ ID NO:27, SEQ ID NO:28 and SEQ ID NO:29, respectively; and light chain CDR1, CDR2, and CDR3 sequences, SEQ ID NO:30, SEQ ID NO:31, and SEQ ID NO:32, respectively.

A pharmaceutical composition comprising an antibody or antigen binding molecule that specifically binds to an epitope of human PAR1, wherein the epitope comprises the amino acid sequence SFLLRNPNDKYEPFWEDEEKNESGLTE (SEQ ID NO:38), or a fragment thereof, and wherein the antibody or antigen binding molecule is a PAR1 antagonist. The embodiments of the antibodies and antibody binding molecules used in the compositions are as described herein.

A method of amelioriating the symptoms of a disease condition mediated by intracellular signaling through PAR1 comprising administering to a subject in need thereof an antibody or antigen binding molecule that specifically binds to an epitope of human PAR1, wherein the epitope comprises the amino acid sequence SFLLRNPNDKYEPFWEDEEKNESGLTE (SEQ ID NO:38), or a fragment thereof, and wherein the antibody or antigen binding molecule is a PAR1 antagonist. The embodiments of the antibodies and antibody binding molecules used in the methods are as described herein.

In some embodiments, the disease condition is mediated by aberrant intracellular signaling through PAR1. In some embodiments, the disease condition is a thrombotic or vascular proliferative disorder. In some embodiments, the disease condition is a cancer that aberrantly expresses PAR1, for example, carcinomas or epithelial cancers, including for example, skin cancers (including melanoma), gastrointestinal cancers (including colon cancer), lung cancer and mammary cancer (including breast and ductal cancers), prostate cancer, endometrial cancer, ovarian cancer, adenocarcinoma, and the like. In some embodiments, the disease condition is a chronic intestinal inflammatory disorder, for example, inflammatory bowel disease (IBD), irritable bowel syndrome (IBS) and ulcerative colitis. In some embodiments, the disease condition is a fibrotic disorder, for example, liver fibrosis and lung fibrosis.

In some embodiments, the disease condition is mediated by intracellular signaling through PAR1 that may or may not be aberrant. In some embodiments, the methods are directed to inhibiting or preventing ischemia-reperfusion injury, including myocardial, renal, cerebral and intestinal ischemia-reperfusion injury. In some embodiments, the methods are directed to inhibiting or preventing herpes simple virus (HSV1 and HSV2) infection of cells.

A further understanding of the nature and advantages of the present invention may be realized by reference to the remaining portions of the specification and claims.

DEFINITIONS

Unless defined otherwise, all technical and scientific terms used herein have the same meaning as commonly understood by those of ordinary skill in the art to which this invention pertains. The following references provide one of skill with a general definition of many of the terms used in this invention: Oxford Dictionary of Biochemistry and Molecular Biology, Smith et al. (eds.), Oxford University Press (revised ed., 2000); Dictionary of Microbiology and Molecular Biology, Singleton et al. (Eds.), John Wiley & Sons (3PrdP ed., 2002); and A Dictionary of Biology (Oxford Paperback Reference), Martin and Hine (Eds.), Oxford University Press (4PthP ed., 2000). In addition, the following definitions are provided to assist the reader in the practice of the invention.

The term "antibody" and "antigen-binding molecule" is used to denote polypeptide chain(s) which exhibit a strong monovalent, bivalent or polyvalent binding to a given epitope or epitopes. Unless otherwise noted, antibodies or antigen-binding molecules of the invention can have sequences derived from any vertebrate, mammalian, camelid, avian or pisces species. They can be generated using any suitable technology, e.g., hybridoma technology, ribosome display, phage display, gene shuffling libraries, semi-synthetic or fully synthetic libraries or combinations thereof. As detailed herein, antibodies or antigen-binding molecules of the invention include intact antibodies, antigen-binding polypeptide chains and other designer antibodies (see, e.g., Serafini, J Nucl Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda, Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The VH and VL regions of an antibody can be further subdivided into regions of hypervariability, also termed complementarity determining regions (CDRs), which are interspersed with the more conserved framework regions (FRs). Each VH and VL is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., Sequences of Proteins of Immunological Interest, U.S. Department of Health and Human Services, U.S. Government Printing Office (1987 and 1991).

Amino acids from the variable regions of the mature heavy and light chains of immunoglobulins are designated Hx and Lx respectively, where x is a number designating the position of an amino acid according to the scheme of Kabat et al, supra. Kabat et al. list many amino acid sequences for antibodies for each subgroup, and lists the most commonly occurring amino acid for each residue position in that subgroup to generate a consensus sequence. Kabat et al. use a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat et al. by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention.

Antibody or antigen-binding molecule also includes antibody fragments which contain the antigen-binding portions of an intact antibody that retain capacity to bind the cognate antigen. Examples of such antibody fragments include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., Nature 341:544-546, 1989), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., Science 242:423-426, 1988; and Huston et al., Proc. Natl. Acad. Sci. USA 85:5879-5883, 1988.

Antibodies or antigen-binding molecules of the invention further includes one or more immunoglobulin chains that are chemically conjugated to, or expressed as, fusion proteins with other proteins. It also includes bispecific antibody. A bispecific or bifunctional antibody is an artificial hybrid antibody having two different heavy/light chain pairs and two different binding sites. Other antigen-binding fragments or antibody portions of the invention include bivalent scFv (diabody), bispecific scFv antibodies where the antibody molecule recognizes two different epitopes, single binding domains (dAbs), and minibodies.

The various antibodies or antigen-binding fragments described herein can be produced by enzymatic or chemical modification of the intact antibodies, or synthesized de novo using recombinant DNA methodologies (e.g., single chain Fv), or identified using phage display libraries (see, e.g., McCafferty et al., Nature 348:552-554, 1990). For example, minibodies can be generated using methods described in the art, e.g., Vaughan and Sollazzo, Comb Chem High Throughput Screen. 4:417-30 2001. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Single chain antibodies can be identified using phage display libraries or ribosome display libraries, gene shuffled libraries. Such libraries can be constructed from synthetic, semi-synthetic or nave and immunocompetent sources.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, as shown in the Examples below, a mouse anti-hPAR1 antibody can be modified by replacing its constant region with the constant region from a human immunoglobulin. Due to the replacement with a human constant region, the chimeric antibody can retain its specificity in recognizing human PAR1 while having reduced antigenicity in human as compared to the original mouse antibody.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc.

Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994.

The term "antibody binding molecule" or "non-antibody ligand" refers to antibody mimics that use non-immunoglobulin protein scaffolds, including adnectins, avimers, single chain polypeptide binding molecules, and antibody-like binding peptidomimetics.

The term "antagonist," as used herein, refers to an agent that is capable of specifically binding and inhibiting signaling through a receptor to fully block or detectably inhibit a response mediated by the receptor. For example, an antagonist of PAR1 specifically binds to the receptor and fully or partially inhibits PAR1-mediated signaling. In some cases, a PAR1 antagonist can be identified by its ability to bind to PAR1 and inhibit thrombin-induced calcium flux or thrombin-induced IL-8 production subsequent to intracellular signaling from a PAR1 (e.g., as measured in a FlipR assay, or by ELISA). Additional assays are described by Kawabata, et al., *J Pharmacol Exp Ther*. (1999) 288(1):358-70. Inhibition occurs when PAR1 intracellular signaling, as measured for example by calcium flux or IL-8 production, from a PAR1 exposed to an antagonist of the invention is at least about 10% less, for example, at least about 25%, 50%, 75% less, or totally inhibited, in comparison to intracellular signaling from a control PAR1 not exposed to an antagonist. A control PAR1 can be exposed to no antibody or antigen binding molecule, an antibody or antigen binding molecule that specifically binds to another antigen, or an anti-PAR1 antibody or antigen binding molecule known not to function as an antagonist. An "antibody antagonist" refers to the situation where the antagonist is an inhibiting antibody.

The term "protease activated receptor-1," "proteinase activated receptor-1," or "PAR1" interchangeably refer to a G-protein-coupled receptor that is activated by thrombin cleavage thereby exposing an N-terminal tethered ligand. PAR1 is also known as "thrombin receptor" and "coagulation factor II receptor precursor." See, for example, Vu, et al., *Cell* (1991) 64(6):1057-68; Coughlin, et al, *J Clin Invest* (1992) 89(2):351-55; and GenBank Accession number NM_001992. Intramolecular binding of the tethered ligand to the extracellular domain of PAR1 elicits intracellular signaling and calcium flux. See, for example, Traynelis and Trejo, *Curr Opin Hematol* (2007) 14(3):230-5; and Hollenberg, et al, *Can J Physiol Pharmacol*. (1997) 75(7):832-41. The nucleotide and amino acid sequences of PAR1 are known in the art. See, for example, Vu, et al., *Cell* (1991) 64(6):1057-68; Coughlin, et al, *J Clin Invest* (1992) 89(2):351-55; and GenBank Accession number NM_001992. The nucleic acid sequence of human PAR1 is published as GenBank accession number NM_001992 (see also, M62424.1 and gi4503636). The amino acid sequence of human PAR1 is published as NP_001983 and AAA36743. As used herein, a PAR1 polypeptide is functionally a G-protein-coupled receptor that is activated by thrombin, and elicits intracellular signaling and calcium flux upon binding of the N-terminal tethered ligand. Structurally, a PAR1 amino acid sequence shares at least about 90%, 91%, 92%, 93%, 94%, 95%, 96%, 97%, 98%, 99% or 100% sequence identity with the amino acid of GenBank accession numbers NP_001983, AAA36743 or M62424.1. Structurally, a PAR1 nucleotide acid sequence shares at least about 90%, 91%, 92%, 93%, 94%, 95%, 96%, 97%, 98%, 99% or 100% sequence identity with the amino acid of GenBank accession numbers NM-001992, or M62424.1.

Binding specificity of an antibody or antigen-binding molecule refers to the ability of the combining site of an individual antibody or antigen-binding molecule to react with only one antigenic determinant. The combining site of a typical antibody is located in the Fab portion of the molecule and is constructed from the hypervariable regions of the heavy and light chains. In some embodiments, binding specificity refers to a particular epitope within a PAR1 polypeptide (e.g., SFLLRNPNDKYEPFWEDEEKNESGLTE, or fragments thereof) preferentially bound by the antibody of the invention. Antibodies that share a binding specificity for a particular epitope will competitively bind to that epitope. Antibodies that competitively bind to a common epitope can displace each other from binding to the common epitope, as measured using any binding assay known in the art, for example, solid phase radio immunoassay (SPRIA) wherein the first competitive antibody or the second competitive antibody is labeled with a radioisotope. Competitive antibodies that share a binding specificity need not bind to identical epitopes, but can bind to overlapping epitopes that allow for competitive displacement in binding assays. In some embodiments, binding specificity refers to the PAR subtype (e.g., PAR1 versus PAR2 or another PAR subtype, for example PAR3 or PAR4) preferentially bound by the antibody of the invention.

Binding affinity is the strength of the reaction between a single antigenic determinant and a single combining site on the antibody or antigen-binding molecule. It is the sum of the attractive and repulsive forces operating between the antigenic determinant and the combining site. Affinity is the equilibrium constant that describes the antigen-antibody reaction.

The phrase "specifically (or selectively) bind to" refers to a preferential binding reaction between an antibody or antigen-binding molecule (e.g., an anti-hPAR1 antibody) and a cognate antigen (e.g., a human PAR1 polypeptide) in a heterogeneous population of proteins and other biologics. The phrases "an antibody recognizing an antigen" and "an antibody specific for an antigen" are used interchangeably herein with the term "an antibody which binds specifically to an antigen". It is recognized that a certain degree of non-specific interaction may occur between an antibody and a non-target epitope. Nevertheless, specific binding, may be distinguished as mediated through specific recognition of the target epitope. Typically specific binding results in a much stronger association between the delivered molecule and an entity (e.g., an assay well or a cell) bearing the target epitope than between the bound antibody and an entity (e.g., an assay well or a cell) lacking the target epitope. Specific binding typically results in greater than about 10-fold and most preferably greater than 100-fold increase in amount of bound anti-PAR1 antibody (per unit time) to a cell or tissue bearing the target epitope as compared to a cell or tissue lacking the target epitope. Specific binding between two entities generally means an affinity of at least $10^6$ $M^{-1}$. Affinities greater than $10^8$ $M^{-1}$ are preferred. Specific binding can be determined using any assay for antibody binding known in the art, including Western Blot, ELISA, flow cytometry, immunohistochemistry.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., Current Protocols in Molecular Biology, John Wiley & Sons, Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compounds or agents to prevent or delay the onset of the symptoms, complications, or biochemical indicia of a disease (e.g., a tumor), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The phrase "signal transduction pathway" or "signaling pathway" (e.g., the PAR1 signaling pathway) refers to at least one biochemical reaction, but more commonly a series of biochemical reactions, which result from interaction of a cell with a stimulatory compound or agent. Thus, the interaction of a stimulatory compound (e.g., thrombin) with a cell generates a "signal" that is transmitted through the signal transduction pathway, ultimately resulting in a cellular response.

BRIEF DESCRIPTION OF THE DRAWINGS

FIG. 1 shows nucleotide sequences of variable regions of mouse anti-hPAR1 antibody clones 4E7.J14.L16 and 6E11.H6.A9 (SEQ ID NOS:1-4). CDR regions are indicated by underlined residues. Framework regions are denoted by the other residues.

FIG. 2 shows amino acid sequences of variable regions of mouse anti-hPAR1 antibody clones 4E7.J14.L16 and 6E11.H6.A9 (SEQ ID NOS:5-8). Underlined sequences denote the CDR regions, while the other sequence portions indicate framework regions.

DETAILED DESCRIPTION

1. Introduction

Figure 3:
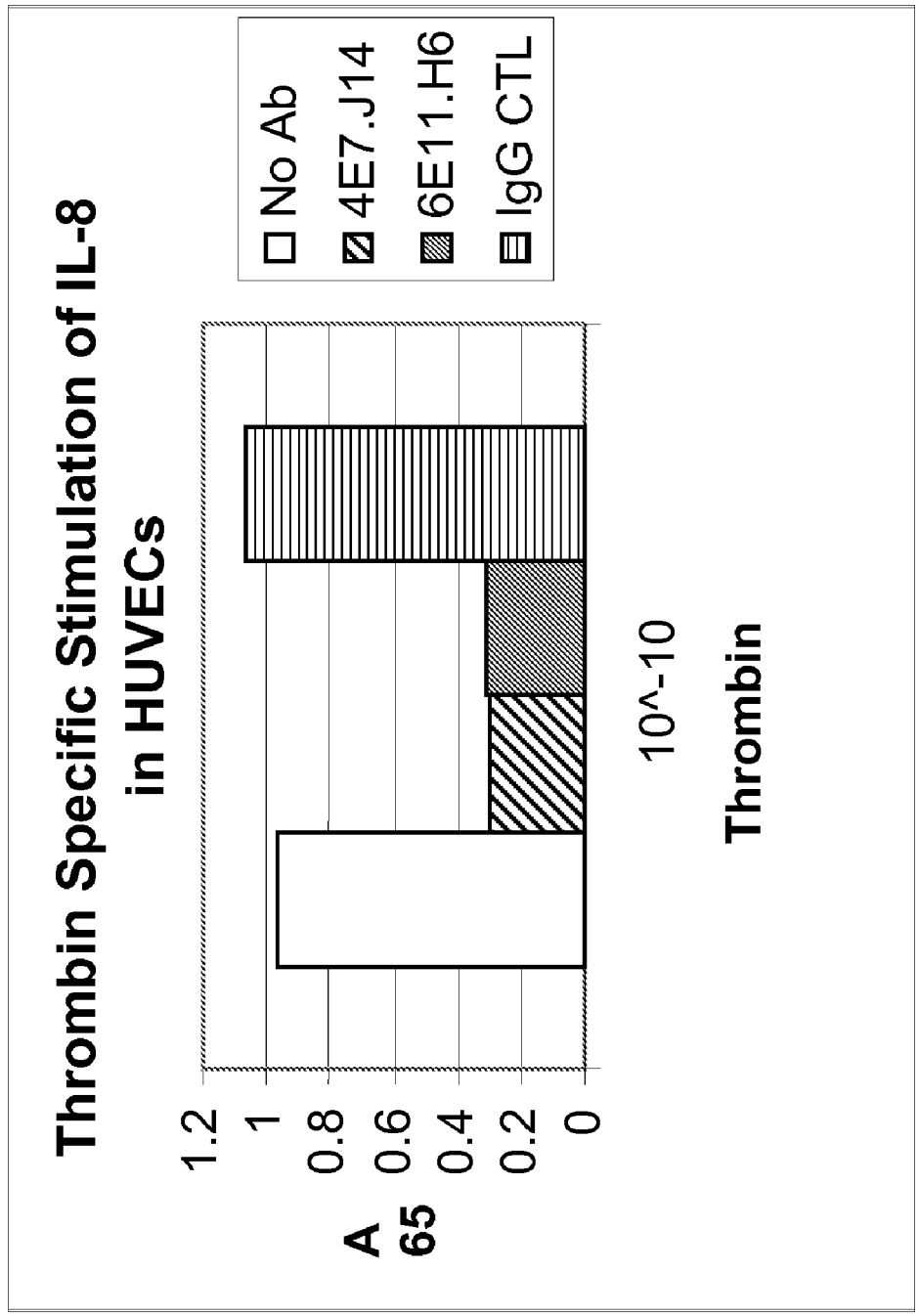
FIG. 3 shows that thrombin stimulated secretion of IL-8 by HUVEC cells is inhibited by mouse anti-hPAR1 antibody clone 4E7.J14.L16 or 6E11.H6.A9.
Figure 4:
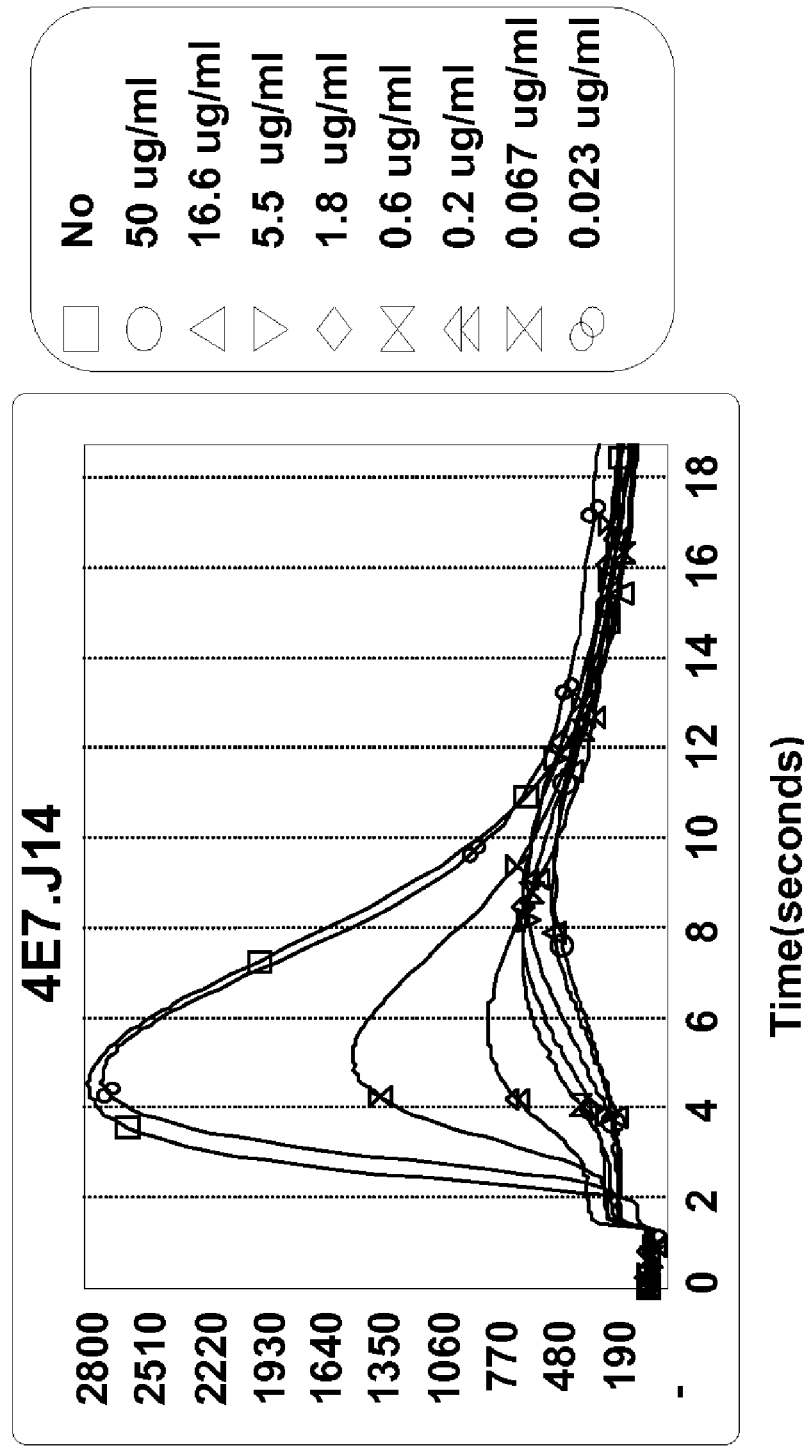
FIG. 4 illustrates the strong antagonist activity of clone 4E7.J14, as measured in a calcium flux (FlipR) assay.
Figure 5:
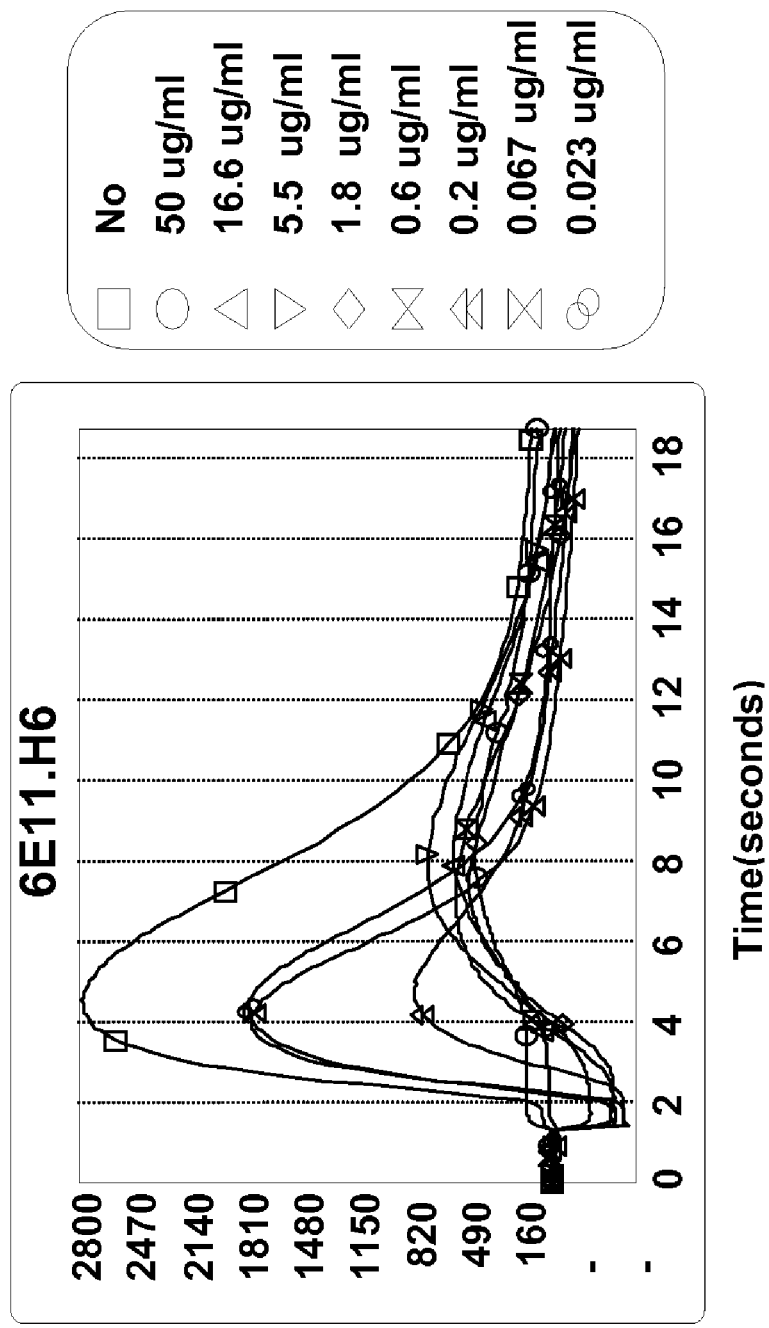
FIG. 5 illustrates the strong antagonist activity of clone 6E11.H6, as measured in a calcium flux (FlipR) assay.

The present invention is predicated in part on the development by the present inventors of antagonist antibodies or antigen-binding molecules against human PAR1. The anti-hPAR1 antibodies generated in mouse or chimeric anti-hPAR1 antibodies created in vitro were able to specifically bind to a human PAR1 polypeptide. In addition, the antibodies were found to be able to inhibit activities mediated by PAR1 signaling, e.g., thrombin-mediated interleukin secretions. Thus, these antibodies are useful as therapeutic or prophylactic agents a number of diseases or disorders mediated by or associated with PAR1 signaling activities, e.g., irritable bowel syndrome or liver fibrosis. The following sections provide guidance for making and using the compositions of the invention.

2. Antagonist Antibodies or Antigen-Binding Molecules of Human PAR1 a. Overview

The invention provides antibodies or antigen-binding molecules that specifically bind to human PAR1. These anti-hPAR1 agents are capable of antagonizing PAR1 mediated signaling activities, e.g., PAR1 mediated interleukin secretion as described in the Examples below. General methods for preparation of monoclonal or polyclonal antibodies are well known in the art. See, e.g., Harlow & Lane, Using Antibodies, A Laboratory Manual, Cold Spring Harbor Laboratory Press, Cold Spring Harbor, N.Y., 1998; Kohler & Milstein, Nature 256:495-497, 1975; Kozbor et al., Immunology Today 4:72, 1983; and Cole et al., pp. 77-96 in Monoclonal Antibodies and Cancer Therapy, 1985.

Preferably, the anti-hPAR1 antibodies of the invention are monoclonal antibodies like the anti-hPAR1 antibody clone 4E7.J14.L16 or clone 6E11.H6.A9 described in the Examples below. Polynucleotide sequences and amino acid sequences of the variable regions of these two exemplified anti-hPAR1 monoclonal antibodies are shown in FIGS. 1 and 2, respectively. Monoclonal antibodies refer to antibodies derived from a single clone. Any technique for producing monoclonal antibody can be employed to produce anti-hPAR1 antibodies of the invention, e.g., viral or oncogenic transformation of B lymphocytes. One animal system for preparing hybridomas is the murine system. Hybridoma production in the mouse is a very well-established procedure. As illustrated in the Examples below, monoclonal anti-hPAR1 antibodies can be generated by immunizing a non-human animal (e.g., mouse) with an hPAR1 polypeptide, or a fragment, fusion protein, or variant thereof. B cells isolated from the animal are then fused to myeloma cells to generate antibody-producing hybridomas. Monoclonal mouse anti-hPAR1 antibodies can be obtained by screening the hybridomas in an ELISA assay using an hPAR1 polypeptide or fusion protein. Immunization protocols and techniques for isolation of immunized splenocytes for fusion are known in the art. Fusion partners (e.g., murine myeloma cells) and fusion procedures are also well known in the art, e.g., Harlow & Lane, supra.

The amino acid sequences of the heavy chain and light chain variable regions of the exemplary mouse anti-PAR1 antibodies (clones 4E7.J14.L16 and 6E11.H6.A9) described in the Examples below are shown in SEQ ID NOS:5-8. The CDR sequences of the heavy chain variable region of clone 4E7.J14.L16 are DYYMN(CDR1; SEQ ID NO:21), VIDPH-NGRSRYNQMFKG (CDR2; SEQ ID NO:22), and DDGP-SHWYFDV (CDR3; SEQ ID NO:23). The CDR sequences of its light chain variable region are RSSQNIVHSNGNTYLE (CDR1; SEQ ID NO:24), KVSNRFS (CDR2; SEQ ID NO:25), and FQGSHVPFT (CDR3; SEQ ID NO:26). The CDR sequences of the heavy chain variable region of clone 6E11.H6.A9 are DHTFH(CDR1; SEQ ID NO:27), YIF-PRDGSTKYNEKFKG (CDR2; SEQ ID NO:28), and HYYGSFEY (CDR3; SEQ ID NO:29). The CDR sequences of its light chain variable region are RSSQSLVHSNGN-TYLH (CDR1; SEQ ID NO:30), KVSNRFS (CDR2; SEQ ID NO:31), and SQSTHLPLT (CDR3; SEQ ID NO:32)

A typical intact antibody interacts with target antigen predominantly through amino acid residues that are located in the six heavy and light chain complimentarity determining regions (CDR's). Typically, the anti-hPAR1 antibodies of the invention have at least one of their heavy chain CDR sequences or light chain CDR sequences identical to the corresponding CDR sequences of anti-PAR1 antibody clone 4E7.J14.L16 or 6E11.H6.A9. Some of these anti-hPAR1 antibodies of the invention have the same binding specificity, and therefore compete with a reference antibody, for an epitope within the PAR1 N-terminal tethered ligand, for example, within the amino acid sequence SFLLRNPNDKYEPF-WEDEEKNESGLTE (SEQ ID NO:38), or fragments thereof, for example, 8, 9, 10, 11, 12, 13, 14, or 15 contiguous amino acids within the foregoing amino acid sequence. Some anti-hPAR1 antibodies of the invention have all CDR sequences in their variable regions of the heavy chain and light chain, respectively, identical to the corresponding CDR sequences anti-PAR1 antibody clone 4E7.J14.L16 or 6E11.H6.A9. Thus, these anti-hPAR1 antibodies can have the three heavy chain CDR sequences respectively identical to SEQ ID NO:21, SEQ ID NO:22, and SEQ ID NO:23, and the three light chain CDR sequences, respectively, identical to SEQ ID NO:24, SEQ ID NO:25, and SEQ ID NO:26. They can also have the three heavy chain CDR sequences, respectively, identical to SEQ ID NO:27, SEQ ID NO:28, and SEQ ID NO:29, and the three light chain CDR sequences, respectively, identical to SEQ ID NO:30, SEQ ID NO:31, and SEQ ID NO:32.

Some of the anti-hPAR1 antibodies of the invention have their entire heavy chain and light chain variable region sequences, respectively, identical to the corresponding variable region sequences of the mouse antibody clone 4E7.J14.L16 or 6E11.H6.A9. In some other embodiments, other than the identical CDR sequences, the antibodies contain amino acid residues in the framework portions of the variable regions that are different from the corresponding amino acid residues of mouse anti-PAR1 antibody clone 4E7.J14.L16 or 6E11.H6.A9 (e.g., some of the humanized anti-hPAR1 antibodies described below). Nevertheless, these antibodies typically have their entire variable region sequences that are substantial identical (e.g., 75%, 85%, 90%, 95%, or 99%) to the corresponding variable region sequences of mouse anti-PAR1 antibody clone 4E7.J14.L16 or clone 6E11.H6.A.

The anti-hPAR1 antibodies of the invention can be an intact antibody which contains two heavy chains and two light chains. They can also be antigen-binding molecules of an intact antibody or single chain antibodies. The anti-hPAR1 antibodies of the invention include antibodies produced in a non-human animal (e.g., the mouse anti-hPAR1 antibody clone 4E7.J14.L16 or 6E11.H6.A). They also include modified antibodies which are modified forms of the mouse anti-hPAR1 antibody clone 4E7.J14.L16 or 6E11.H6.A. Often, the modified antibodies are recombinant antibodies which have similar or improved properties relative to that of the exemplified mouse antibody. For example, the mouse anti-hPAR1 antibody exemplified in the Examples below can be modified by deleting the constant region and replacing it with a different constant region that can lead to increased half-life, e.g., serum half-life, stability or affinity of the antibody. The modified antibodies can be created, e.g., by constructing expression vectors that include the CDR sequences from the mouse antibody grafted onto framework sequences from a different antibody with different properties (Jones et al. 1986, Nature 321, 522-525). Such framework sequences can be obtained from public DNA databases (e.g., on the worldwide web at kabatdatabase.com).

Some of the modified antibodies are chimeric antibodies which contain partial human immunoglobulin sequences (e.g., constant regions) and partial non-human immunoglobulin sequences (e.g., the mouse anti-hPAR1 antibody variable region sequences of mouse anti-hPAR1 antibody clone 4E7.J14.L16 or 6E11.H6.A). Some other modified antibodies are humanized antibodies. Generally, a humanized antibody has one or more amino acid residues introduced into it from a source that is non-human. Methods for humanizing non-human antibodies are well known in the art, e.g., U.S. Pat. Nos. 5,585,089 and 5,693,762; Jones et al., Nature 321: 522-25, 1986; Riechmann et al., Nature 332: 323-27, 1988; and Verhoeyen et al., Science 239: 1534-36, 1988. These methods can be readily employed to generate humanized anti-hPAR1 antibodies of the invention by substituting at least a portion of a CDR from a non-human anti-hPAR1 antibody for the corresponding regions of a human antibody. In some embodiments, the humanized anti-hPAR1 antibodies of the invention have all three CDRs in each immunoglobulin chain from the mouse anti-hPAR1 antibody clone 4E7.J14.L16 or 6E11.H6.A 5 grafted into corresponding human framework regions.

The anti-hPAR1 antibodies described above can undergo non-critical amino-acid substitutions, additions or deletions in both the variable and constant regions without loss of binding specificity or effector functions, or intolerable reduction of binding affinity. Usually, antibodies incorporating such alterations exhibit substantial sequence identity to a reference antibody (e.g., the mouse anti-hPAR1 antibody clone 4E7.J14.L16 or 6E11.H6.A) from which they were derived. For example, the mature light chain variable regions of some of the anti-hPAR1 antibodies of the invention have at least 75% or at least 85% sequence identity to the sequence of the mature light chain variable region of the exemplified mouse anti-hPAR1 antibodies. Similarly, the mature heavy chain variable regions of the antibodies typically show at least 75% or at least 85% sequence identity to the sequence of the mature heavy chain variable region of the exemplified anti-hPAR1 antibodies. Some of the modified anti-hPAR1 antibodies have the same specificity and increased affinity compared with the exemplified mouse anti-hPAR1 antibodies. Usually, the affinity of the modified anti-hPAR1 antibodies is within a factor of 2, 5, 10 or 50 of the reference mouse anti-hPAR1 antibody.

b. Chimeric and Humanized Anti-hPAR1 Antibodies

Some of the anti-hPAR1 antibodies of the invention are chimeric (e.g., mouse/human) antibodies which are made up of regions from a non-human anti-hPAR1 antibody antagonist together with regions of human antibodies. For example, a chimeric H chain can comprise the antigen binding region of the heavy chain variable region of the mouse anti-PAR1 antibody exemplified herein (e.g., SEQ ID NO:5 or 7) linked to at least a portion of a human heavy chain constant region. This chimeric heavy chain may be combined with a chimeric L chain that comprises the antigen binding region of the light chain variable region of the exemplified mouse anti-hPAR1 antibody (e.g., SEQ ID NO:6 or 8) linked to at least a portion of the human light chain constant region.

Chimeric anti-hPAR1 antibodies of the invention can be produced in accordance with the disclosure in the Examples below as well as methods known in the art. For example, a gene encoding the heavy chain or light chain of a murine anti-hPAR1 antibody or antigen-binding molecule can be digested with restriction enzymes to remove the murine Fc region, and substituted with the equivalent portion of a gene encoding a human Fc constant region. Expression vectors and host cells suitable for expression of recombinant antibodies and humanized antibodies in particular, are well known in the art. Vectors expressing chimeric genes encoding anti-hPAR1 immunoglobulin chains can be constructed using standard recombinant techniques, e.g., Sambrook et al., Molecular Cloning: A Laboratory Manual, Cold Spring Harbor Press (3rd ed., 2001); and Brent et al., Current Protocols in Molecular Biology, John Wiley & Sons, Inc. (ringbou ed., 2003). Human constant region sequences can be selected from various reference sources, including but not limited to those listed in Kabat et al., Sequences of Proteins of Immunological Interest, Fifth Edition, U.S. Department of Health and Human Services, U.S. Government Printing Office, 1991. More specific teachings of producing chimeric antibodies by DNA recombination have also been taught in the art, e.g., Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., Science 240:1041-1043, 1988; Liu et al., PNAS 84:3439-3443, 1987; Liu et al., J. Immunol. 139:3521-3526, 1987; Sun et al., PNAS 84:214-218, 1987; Nishimura et al., Canc. Res. 47:999-1005, 1987; Wood et al., Nature 314:446-449, 1985; Shaw et al., J. Natl. Cancer Inst. 80:1553-1559, 1988.

Chimeric antibodies which have the entire variable regions from a non-human antibody can be further humanized to reduce antigenicity of the antibody in human. This is typically accomplished by replacing certain sequences or amino acid residues in the Fv variable regions (framework regions or non-CDR regions) with equivalent sequences or amino acid residues from human Fv variable regions. These additionally substituted sequences or amino acid residues are usually not directly involved in antigen binding. More often, humanization of a non-human antibody proceeds by substituting only the CDRs of a non-human antibody (e.g., the mouse anti-PAR1 antibodies exemplified herein) for the CDRs in a human antibody. In some cases, this is followed by replacing some additional residues in the human framework regions with the corresponding residues from the non-human donor antibody. Such additional grafting is often needed to improve binding to the antigen. This is because humanized antibodies which only have CDRs grafted from a non-human antibody can have less than perfect binding activities as compared to that of the non-human donor antibody. Thus, in addition to the CDRs, humanized anti-hPAR1 antibodies of the invention can often have some amino acids residues in the human framework region replaced with corresponding residues from the non-human donor antibody (e.g., the mouse antibody exemplified herein). Methods for generating humanized antibodies by CDR substitution, including criteria for selecting framework residues for replacement, are well known in the art. For example, in addition to the above noted art relating to producing chimeric antibodies, additional teachings on making humanized antibodies are provided in, e.g., Winter et al., UK Patent Application GB 2188638A (1987), U.S. Pat. No. 5,225,539; Jones et al., Nature 321:552-525, 1986; Verhoeyan et al., Science 239:1534, 1988; and Beidler et al., J. Immunol. 141:4053-4060, 1988. CDR substitution can also be carried out using oligonucleotide site-directed mutagenesis as described in, e.g., WO 94/10332 entitled "Humanized Antibodies to Fc Receptors for Immunoglobulin G on Human Mononuclear Phagocytes."

The chimeric or humanized anti-hPAR1 antibodies of the invention may be monovalent, divalent, or polyvalent immunoglobulins. For example, a monovalent chimeric antibody is a dimer (HL) formed by a chimeric H chain associated through disulfide bridges with a chimeric L chain, as noted above. A divalent chimeric antibody is a tetramer (H2 L2) formed by two HL dimers associated through at least one disulfide bridge. A polyvalent chimeric antibody is based on an aggregation of chains.

c. Human Anti-hPAR1 Antibodies

In addition to chimeric or humanized anti-hPAR1 antibodies, also included in the invention are fully human antibodies that exhibit the same binding specificity and comparable or better binding affinity. For example, the human anti-hPAR1 antibodies can have the same or better binding characteristics (e.g., binding specificity and/or binding affinity) relative to that of a reference nonhuman anti-PAR1 antibody, e.g., mouse anti-hPAR1 antibody clone 4E7.J14.L16 or 6E1.H6.A. The reference nonhuman antibody can be the mouse anti-PAR1 antibody which contains a heavy chain variable region sequence of SEQ ID NO:5 and a light chain variable region sequence of SEQ ID NO:6. It can also be the mouse anti-PAR1 antibody which contains a heavy chain variable region sequence of SEQ ID NO:7 and a light chain variable region sequence of SEQ ID NO:8. Compared to the chimeric or humanized antibodies, the human anti-hPAR1 antibodies of the invention have further reduced antigenicity when administered to human subjects.

The human anti-hPAR1 antibodies can be generated using methods that are known in the art. For example, an in vivo method for replacing a nonhuman antibody variable region with a human variable region in an antibody while maintaining the same or providing better binding characteristics relative to that of the nonhuman antibody has been disclosed in U.S. patent application Ser. No. 10/778,726 (Publication No. 20050008625). The method replies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("test antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No. 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric anti-hPAR1 antibodies described above as the reference antibody, this method can be readily employed to generate human antibodies that bind to human PAR1 with the same binding specificity and the same or better binding affinity. In addition, such human anti-hPAR1 antibodies can also be commercially obtained from companies which customarily produce human antibodies, e.g., KaloBios, Inc. (Mountain View, Calif.). To obtain human antibodies with the same or better affinities for a specific epitope than a starting non-human antibody (e.g., a mouse anti-PAR1 antibody), the KaloBios, Inc. technologies employ a human "acceptor" antibody library. A directed or epitope focused library of human antibodies which bind to the identical epitope as the non-human antibody, though with varying affinities, is then generated. Antibodies in the epitope focused library are then selected for similar or higher affinity than that of the starting non-human antibody. The identified human antibodies are then subject to further analysis for affinity and sequence identity.

d. Other Types of Anti-hPAR1 Antibodies

The anti-hPAR1 antibodies or antigen-binding molecules of the invention also include single chain antibodies, bispecific antibodies and multi-specific antibodies. In some embodiments, the antibodies of the invention are single chain antibodies. Single chain antibodies contain in a single stably-folded polypeptide chain the antigen-binding regions from both the heavy chain and the light chain. As such, single chain antibodies typically retain the binding specificity and affinity of monoclonal antibodies but are of considerably small size than classical immunoglobulins. For certain applications, the anti-hPAR1 single chain antibodies of the invention may provide many advantageous properties as compared to an intact anti-hPAR1 antibody. These include, e.g., faster clearance from the body, greater tissue penetration for both diagnostic imaging and therapy, and a significant decrease in immunogenicity when compared with mouse-based antibodies. Other potential benefits of using single chain antibodies include enhanced screening capabilities in high throughput screening methods and the potential for non-parenteral application.

Single chain anti-hPAR1 antibodies of the invention can be prepared using methods that have been described in the art. Examples of such techniques include those described in U.S. Pat. Nos. 4,946,778 and 5,258,498; Huston et al., Methods in Enzymology 203:46-88, 1991; Shu et al., Proc. Natl. Acad. Sci. USA 90:7995-7999, 1993; and Skerra et al., Science 240:1038-1040, 1988.

In some embodiments, the invention provides anti-hPAR1 antibodies derivatized or linked to another functional molecule to generate a bispecific or multispecific molecule which binds to multiple binding sites or target epitopes. The functional molecule includes another peptide or protein (e.g., a cytokine, a cytotoxic agent, an immune stimulatory or inhibitory agent, a Fab' fragment or other antibody binding fragment as discussed above). For example, an anti-hPAR1 antibody or antigen-binding portion thereof can be functionally linked (e.g., by chemical coupling, genetic fusion, noncovalent association or otherwise) to one or more other binding molecules, such as another antibody, antibody fragment, peptide or binding mimetic. Thus, the bispecific and multispecific anti-hPAR1 antibodies of the invention comprises at least one monoclonal anti-hPAR1 antibody or antigen binding fragment thereof with a first binding specificity for human PAR1 and a second binding specificity for a second target epitope. The second target epitope can be an Fc receptor, e.g., human FcγRI or a human Fcγ receptor. Therefore, the invention includes bispecific and multispecific molecules capable of binding both to FcγR1, FcγR or FcεR expressing effector cells (e.g., monocytes, macrophages or polymorphonuclear cells (PMNs)), and to target cells expressing human PAR1 (e.g., cancer cells). These multi-specific (e.g., bispecific or multispecific) molecules target human PAR1 expressing cells to effector cells, and trigger Fc receptor-mediated effector cell activities, such as phagocytosis of a human PAR1-expressing cells, antibody dependent cell-mediated cytotoxicity (ADCC), cytokine release, or generation of superoxide anion.

Bispecific and multispecific anti-hPAR1 molecules of the present invention can be made by methods that have been described in the art. These include chemical techniques (see, e.g., Kranz et al., Proc. Natl. Acad. Sci. USA 78:5807, 1981), polydoma techniques (see, e.g., U.S. Pat. No. 4,474,893), or recombinant DNA techniques. Bispecific and multispecific molecules of the present invention can also be prepared by conjugating the constituent binding specificities, e.g., the anti-FcR and anti-hPAR1 binding specificities, using methods known in the art and as described herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), N-succinimidyl-3-(2-pyridyldithio)propionate (SPDP), and sulfosuccinimidyl 4-(N-maleimidomethyl)cyclohaxane-1-carboxylate (sulfo-SMCC). When the binding specificities are antibodies (e.g., two humanized antibodies), they can be conjugated via sulfhydryl bonding of the C-terminus hinge regions of the two heavy chains. The hinge region can be modified to contain an odd number of sulfhydryl residues, e.g., one, prior to conjugation.

Binding of the bispecific and multispecific molecules to their specific targets can be confirmed by enzyme-linked immunosorbent assay (ELISA), a radioimmunoassay (RIA), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, e.g., Weintraub, B., Principles of Radioimmunoassays, Seventh Training Course on Radioligand Assay Techniques, The Endocrine Society, March, 1986). The radioactive isotope can be detected by such means as the use of a gammas-counter or a scintillation counter or by autoradiography.

Anti-hPAR1 antibodies or antigen-binding molecules of the invention also include single domain antigen-binding units which have a camelid scaffold. Animals in the camelid family include camels, llamas, and alpacas. Camelids produce functional antibodies devoid of light chains. The heavy chain variable (VH) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies. Camelid scaffold-based anti-PAR1 molecules with binding specificities of the mouse anti-PAR1 antibodies exemplified herein can be produced using methods well known in the art, e.g., Dumoulin et al., Nature Struct. Biol. 11:500-515, 2002; Ghahroudi et al., FEBS Letters 414: 521-526, 1997; and Bond et al., Mol. Biol. 332:643-55, 2003.

e. Non-Antibody Ligands that Specifically Bind hPAR1

The anti-PAR1 antibodies or antigen-binding molecules of the invention also include monobodies which are small antibody mimics using the scaffold of a fibronectin type III domain (FN3). Fibronectin is a large protein which plays essential roles in the formation of the extracellular matrix and cell-cell interactions. It consists of many repeats of three types (I, II and III) of small domains. FN3 itself is the paradigm of a large subfamily (FN3 family or s-type immunoglobulin family) of the immunoglobulin superfamily. The FN3 family includes cell adhesion molecules, cell surface hormone and cytokine receptors, chaperonins, and carbohydrate binding domains. FN3 scaffold functions as an effective framework onto which loops for specific building functions can be grafted. There are 15 repeating units of FN3 in human fibronectin. Typically, such antigen-binding molecules of the invention utilize the tenth FN3 unit of human fibronectin as scaffold. It is small, monomeric, and does not have disulfide bonds. FN3 based antigen-binding molecules which exhibit the same binding specificity as the mouse anti-PAR1 antibodies exemplified herein can be prepared using methods described in the art, e.g., Koide et al., J. Mol. Biol. 284: 1141-1151, 1998; Koide et al., Proc. Natl. Acad. Sci. USA 99:1253-1258, 2002; and Batori et al., Protein Eng. 15:1015-20, 2002. See also, U.S. Pat. Nos. 6,818,418 and 7,115,396.

Some other antigen-binding molecules of the invention employ a scaffold derived from A-domains. A-domains occur as strings of multiple domains in several cell-surface receptors. Domains of this family bind many known targets, including small molecules, proteins and viruses. Truncation analysis has shown that a target is typically contacted by multiple A-domains with each domain binding independently to a unique epitope. The avidity generated by combining multiple binding domains is a powerful approach to increase affinity and specificity. Such antigen-binding molecules that bind to PAR1 with the binding specificities of the mouse anti-PAR1 antibodies exemplified herein can be generated using methods described in, e.g., Gliemann et al., Biol. Chem. 379:951-964, 1998; Koduri et al., Biochemistry 40:12801-12807, 2001 and Silverman et al., Nat Biotechnol. 23:1556-61, 2005.

Other compounds have been developed that target and bind to targets in a manner similar to antibodies. Certain of these "antibody mimics" use non-immunoglobulin protein scaffolds as alternative protein frameworks for the variable regions of antibodies.

For example, Ladner et al. (U.S. Pat. No. 5,260,203) describe single polypeptide chain binding molecules with binding specificity similar to that of the aggregated, but molecularly separate, light and heavy chain variable region of antibodies. The single-chain binding molecule contains the antigen binding sites of both the heavy and light variable regions of an antibody connected by a peptide linker and will fold into a structure similar to that of the two peptide antibody. The single-chain binding molecule displays several advantages over conventional antibodies, including, smaller size, greater stability and are more easily modified.

Ku et al. (Proc. Natl. Acad. Sci. U.S.A. 92(14):6552-6556 (1995)) discloses an alternative to antibodies based on cytochrome b562. Ku et al. (1995) generated a library in which two of the loops of cytochrome b562 were randomized and selected for binding against bovine serum albumin. The individual mutants were found to bind selectively with BSA similarly with anti-BSA antibodies.

Beste et al. (Proc. Natl. Acad. Sci. U.S.A. 96(5):1898-1903 (1999)) discloses an antibody mimic based on a lipocalin scaffold (Anticalin®). Lipocalins are composed of a β-barrel with four hypervariable loops at the terminus of the protein. Beste (1999), subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that Anticalin® would be suitable to be used as an alternative to antibodies.

Anticalins® are small, single chain peptides, typically between 160 and 180 residues, which provides several advantages over antibodies, including decreased cost of production, increased stability in storage and decreased immunological reaction.

Hamilton et al. (U.S. Pat. No. 5,770,380) discloses a synthetic antibody mimic using the rigid, non-peptide organic scaffold of calixarene, attached with multiple variable peptide loops used as binding sites. The peptide loops all project from the same side geometrically from the calixarene, with respect to each other. Because of this geometric confirmation, all of the loops are available for binding, increasing the binding affinity to a ligand. However, in comparison to other antibody mimics, the calixarene-based antibody mimic does not consist exclusively of a peptide, and therefore it is less vulnerable to attack by protease enzymes. Neither does the scaffold consist purely of a peptide, DNA or RNA, meaning this antibody mimic is relatively stable in extreme environmental conditions and has a long life span. Further, since the calixarene-based antibody mimic is relatively small, it is less likely to produce an immunogenic response.

Murali et al. (Cell. Mol. Biol. 49(2):209-216 (2003)) discusses a methodology for reducing antibodies into smaller peptidomimetics, they term "antibody like binding peptidomemetics" (ABiP) which can also be useful as an alternative to antibodies.

3. Polynucleotides, Vectors and Host Cells for Producing Anti-hPAR1 Antibodies

The invention provides substantially purified polynucleotides (DNA or RNA) which encode polypeptides comprising segments or domains of the anti-hPAR1 antibody chains or antigen-binding molecules described above. Some of the polynucleotides of the invention comprise the nucleotide sequence of the heavy chain variable region shown in SEQ ID NO: 1 or 3 and/or the nucleotide sequence of the light chain variable region shown in SEQ ID NO:2 or 4. Some other polynucleotides of the invention comprise nucleotide sequences that are substantially identical (e.g., at least 65, 80%, 95%, or 99%) to one of the nucleotide sequences shown in SEQ ID NOS: 1-4. When expressed from appropriate expression vectors, polypeptides encoded by these polynucleotides are capable of exhibiting antigen binding capacity.

Also provided in the invention are polynucleotides which encode at least one CDR region and usually all three CDR regions from the heavy or light chain of the mouse anti-hPAR1 antibodies described in the Examples below. Some other polynucleotides encode all or substantially all of the variable region sequence of the heavy chain and/or the light chain of the mouse anti-hPAR1 antibodies. For example, some of these polynucleotides encode the amino acid sequence of the heavy chain variable region shown in SEQ ID NO:5 or 7 and/or the amino acid sequence of the light chain variable region shown in SEQ ID NO:6 or 8. Because of the degeneracy of the code, a variety of nucleic acid sequences will encode each of the immunoglobulin amino acid sequences.

The polynucleotides of the invention can encode only the variable region sequence of an anti-hPAR1 antibody. They can also encode both a variable region and a constant region of the antibody. Some of polynucleotide sequences of the invention nucleic acids encode a mature heavy chain variable region sequence that is substantially identical (e.g., at least 80%, 90%, or 99%) to the mature heavy chain variable region sequence shown in SEQ ID NO:5 or 7. Some other polynucleotide sequences encode a mature light chain variable region sequence that is substantially identical to the mature light chain variable region sequence shown in SEQ ID NO:6 or 8. Some of the polynucleotide sequences encode a polypeptide that comprises variable regions of both the heavy chain and the light chain of one of the exemplified mouse anti-PAR1 antibody. Some other polynucleotides encode two polypeptide segments that respectively are substantially identical to the variable regions of the heavy chain and the light chain of one of the mouse antibodies.

The polynucleotide sequences can be produced by de novo solid-phase DNA synthesis or by PCR mutagenesis of an existing sequence (e.g., sequences as described in the Examples below) encoding an anti-hPAR1 antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the anti-hPAR1 antibodies described above. Various expression vectors can be employed to express the polynucleotides encoding the anti-PAR1 antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the anti-hPAR1 polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an anti-hPAR1 antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an anti-hPAR1 antibody chain or fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted anti-hPAR1 antibody sequences. More often, the inserted anti-hPAR1 antibody sequences are linked to a signal sequences before inclusion in the vector. Vectors to be used to receive sequences encoding anti-hPAR1 antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the anti-hPAR1 antibody chains can be either prokaryotic or eukaryotic. E. coli is one prokaryotic host useful for cloning and expressing the polynucleotides of the present invention. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express anti-hPAR1 polypeptides of the invention. Insect cells in combination with baculovirus vectors can also be used.

In some preferred embodiments, mammalian host cells are used to express and produce the anti-hPAR1 polypeptides of the present invention. For example, they can be either a hybridoma cell line expressing endogenous immunoglobulin genes (e.g., the myeloma hybridoma clones as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer (see, e.g., Queen et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express anti-hPAR1 antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

4. Properties of Anti-hPAR1 Antibodies or Antigen-Binding Molecules

Once an anti-hPAR1 antibody or antigen-binding molecule described above is synthesized or expressed from an expression vector in a host cell or endogenously in a hybridoma, they can be readily purified from, e.g., culture media and host cells. Usually, antibody chains are expressed with signal sequences and are thus released to the culture media. However, if antibody chains are not naturally secreted by host cells, the antibody chains can be released by treatment with mild detergent. Antibody chains can then be purified by conventional methods including ammonium sulfate precipitation, affinity chromatography to immobilized target, column chromatography, gel electrophoresis and the like. These methods are all well known and routinely practiced in the art, e.g., Scopes, Protein Purification, Springer-Verlag, NY, 1982; and Harlow & Lane, supra.

By way of example, selected hybridomas expressing anti-hPAR1 antibodies of the invention can be grown in spinner-flasks for monoclonal antibody purification. Supernatants can be filtered and concentrated by affinity chromatography with protein A-sepharose or protein G-sepharose columns. IgG molecules eluted from the columns can be examined by gel electrophoresis and high performance liquid chromatography to ensure purity. The buffer solution can be exchanged into PBS, and the concentration can be determined by OD280 reading. The monoclonal antibodies can be aliquoted and stored at −80° C.

Irrespective of their method of preparation, the anti-hPAR1 antibodies or antigen-binding molecules of the present invention bind specifically to hPAR1 or an antigenic fragment thereof. Specific binding exists when the dissociation constant for antibody binding to hPAR1 or an antigenic fragment thereof is $\leq 1$ μM, preferably $\leq 100$ nM, and most preferably $\leq 1$ nM. The ability of an antibody to bind to hPAR1 can be detected by labeling the antibody of interest directly, or the antibody may be unlabelled and binding detected indirectly using various sandwich assay formats. See, e.g., Harlow & Lane, supra. Antibodies having such binding specificity are more likely to share the advantageous properties exhibited by the mouse or chimeric anti-hPAR1 antibodies discussed in the Examples below. Typically, the anti-PAR1 antibodies or antigen-binding molecules of the invention bind to a PAR1 polypeptide or antigenic fragment with an equilibrium association constant ($K_A$) of at least $1 \times 10^7 \, M^{-1}$, $10^8 \, M^{-1}$, $10^9 \, M^{-1}$, or $10^{10} \, M^{-1}$. In addition, they also have a kinetic dissociation constant ($k_d$) of about $1 \times 10^{-3} \, s^{-1}$, $1 \times 10^{-4} \, s^{-1}$, $1 \times 10^{-5} \, s^{-1}$ or lower, and binds to human PAR1 with an affinity that is at least two-fold greater than its affinity for binding to a non-specific antigen (e.g., BSA).

In some embodiments, the anti-hPAR1 antibodies or antigen-binding molecules of the invention block or compete with binding of a reference anti-hPAR1 antibody to an hPAR1 polypeptide. The reference anti-hPAR1 antibody can have heavy chain and light chain variable region sequences shown in SEQ ID NOS:5 and 6 or SEQ ID NOS:7 and 8, e.g., the mouse anti-PAR1 antibodies or chimeric antibodies thereof described in the Examples below. These can be fully human anti-hPAR1 antibodies described above. They can also be other mouse, chimeric or humanized anti-hPAR1 antibodies which bind to the same epitope as the reference antibody. The capacity to block or compete with the reference antibody binding to hPAR1 indicates that an anti-hPAR1 antibody or antigen-binding molecule under test binds to the same or similar epitope as that defined by the reference antibody, or to an epitope which is sufficiently proximal to the epitope bound by the reference anti-hPAR1 antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen (e.g., a PAR1 polypeptide) or epitope on the antigen. A test antibody competes with the reference antibody for specific binding to the antigen or epitope if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of a test anti-hPAR1 antibody or antigen-binding molecule with the reference anti-hPAR1 antibody for binding to human PAR1. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using 1-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing the antigen, an unlabelled test anti-hPAR1 antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if a test anti-PAR1 antibody or antigen-binding molecule and a reference anti-PAR1 antibody bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using a PAR1 polypeptide coated-ELISA plates. Biotinylated MAb binding can be detected with a strep-avidin-alkaline phosphatase probe. To determine the isotype of a purified anti-PAR1 antibody, isotype ELISAs can be performed. For example, wells of microtiter plates can be coated with 1 µg/ml of anti-human IgG overnight at 4° C. After blocking with 1% BSA, the plates are reacted with 1 µg/ml or less of the monoclonal anti-hPAR1 antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal anti-hPAR1 antibodies or antigen-binding molecules to live cells expressing an hPAR1 polypeptide, flow cytometry can be used. Briefly, cell lines expressing hPAR1 (grown under standard growth conditions) can be mixed with various concentrations of an anti-hPAR1 antibody in PBS containing 0.1% BSA and 10% fetal calf serum, and incubated at 37° C. for 1 hour. After washing, the cells are reacted with fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained as described above and examined by fluorescence microscopy.

Anti-hPAR1 antibodies of the invention can be further tested for reactivity with an hPAR1 polypeptide or antigenic fragment by immunoblotting. Briefly, purified hPAR1 polypeptides or fusion proteins, or cell extracts from cells expressing PAR1 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

5. Therapeutic Applications and Pharmaceutical Compositions

The anti-hPAR1 antibodies or antigen-binding molecules described herein can be employed in many therapeutic or prophylactic applications by inhibiting PAR1 signaling activities. In therapeutic applications, a composition comprising an anti-hPAR1 antagonist antibody or antigen-binding molecule (e.g., a humanized anti-hPAR1 antibody) is administered to a subject already affected by a disease or condition mediated by, caused by or associated with PAR1 signaling. The composition contains the antibody or antigen-binding molecule in an amount sufficient to inhibit, partially arrest, or detectably slow the progression of the condition, and its complications.

In prophylactic applications, compositions containing the anti-hPAR1 antibodies or antigen-binding molecules are administered to a patient not already suffering from a PAR1-signaling related disorder. Rather, they are directed to a subject who is at the risk of, or has a predisposition, to developing such a disorder. Such applications allow the subject to enhance the patient's resistance or to retard the progression of a disorder mediated by PAR1 signaling.

Numerous disease conditions are mediated by aberrant or abnormally high PAR1-mediated intracellular signaling. Abnormally high PAR1-mediated intracellular signaling can be the caused by, for example, exposure of the receptor to abnormally high concentrations of an activating protease (e.g., thrombin) or abnormally high cell surface expression levels of PAR1. Inhibition of PAR1 is helpful for treating thrombotic and vascular proliferative disorders as well as for inhibiting progression of cancers. See, for example, Darmoul, et al., *Mol Cancer Res* (2004) 2(9):514-22 and Salah, et al, *Mol Cancer Res* (2007) 5(3):229-40. Inhibiting PAR1 also finds use in preventing or inhibiting chronic intestinal inflammatory disorders, including inflammatory bowel disease (IBD), irritable bowel syndrome (IBS) and ulcerative colitis; and fibrotic disorders, including liver fibrosis and lung fibrosis. See, for example, Vergnolle, et al., *J Clin Invest* (2004) 114(10): 1444; Yoshida, et al, *Aliment Pharmacol Ther* (2006) 24(Suppl 4):249; Mercer, et al., *Ann NY Acad Sci* (2007) 1096:86-88; Sokolova and Reiser, *Pharmacol Ther* (2007) PMID:17532472.

Cancers that can be inhibited or prevented by the anti-PAR1 antibodies or antigen-binding molecules of the invention include, without limitation, epithelial cancers including carcinomas; gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non- Hodgkin's lymphoma (see, CANCER: PRINCIPLES AND PRACTICE (DeVita, V. T. et al. eds 1997) for additional cancers).

Inhibiting PAR1 also finds use in preventing or inhibiting disease conditions that may or may not be mediated by aberrant or abnormally high PAR1 expression or intracellular signaling. For example, inhibiting PAR1 is useful for preventing or inhibiting ischemia-reperfusion injury, including myocardial, renal, cerebral and intestinal ischemia-reperfusion injury. See, for example, Strande, et al., *Basic Res. Cardiol* (2007) 102(4):350-8; Sevastos, et al., *Blood* (2007) 109(2): 577-583; Junge, et al., *Proc Natl Acad Sci USA*. (2003) 100 (22):13019-24 and Tsuboi, et al., *Am J Physiol Gastrointest Liver Physiol* (2007) 292(2):G678-83. Inhibiting PAR1 intracellular signaling can also be used to inhibit herpes simple virus (HSV1 and HSV2) infection of cells. See, Sutherland, et al., *J Thromb Haemost* (2007) 5(5):1055-61.

The invention provides pharmaceutical compositions comprising the anti-hPAR1 antibodies or antigen-binding molecules formulated together with a pharmaceutically acceptable carrier. The compositions can additionally contain other therapeutic agents that are suitable for treating or preventing a given disorder. Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

In some embodiments, the composition is sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the anti-hPAR1 antibody is employed in the pharmaceutical compositions of the invention. The anti-hPAR1 antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

Antibody is usually administered on multiple occasions. Intervals between single dosages can be weekly, monthly or yearly. Intervals can also be irregular as indicated by measuring blood levels of anti-hPAR1 antibody in the patient. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

EXAMPLES

The following examples are provided to further illustrate the invention but not to limit its scope. Other variants of the invention will be readily apparent to one of ordinary skill in the art and are encompassed by the appended claims.

Example 1

Development of Mouse Anti-hPAR1 Antagonist Antibodies

This Example describes the development of mouse anti-hPAR1 antagonist antibodies. Bcl2 Wehi22 mice were immunized with human PAR1 (AA #27-102)/thioredoxin fusion protein. The immunization was carried out 8 times over 18 days. B-cells were isolated from peripheral lymph nodes and fused to F0 myeloma cells (ATCC, Manassas, Va.). Antibody production was screened by ELISA against hPAR1/thioredoxin fusion protein. A total of 10 clones were obtained which produce antibodies that specifically recognize hPAR1. Binding of hPAR1 antibodies to cell surface PAR1 was analyzed using cell ELISA on HT29 cells (PAR1 positive) and colo205 cells (PAR1 negative). Briefly, cells were incubated with hybridoma culture supernatants followed by HRP-conjugated anti-mouse IgG. TMB substrate (KPL, Gaithersburg, Md.) was added, 20 minutes later wells were acidified with sulfuric acid (2N) and color was measured at 450 nm. The results showed that 5 hybridoma clones out of 10 clones were able to bind to the cell surface receptor.

Monoclonal antibody (mAb) from each of the cell binding positives clones was purified. Briefly, serum-free conditioned medium was purified over Protein G resin (Amersham Biosciences, Piscataway, N.J.). In addition, the 10 antibody producing clones were subcloned by limiting dilution, and the resulting clones were evaluated for PAR1 binding via ELISA and cell ELISA. The functional subclones were also evaluated for functionality as described below.

An hPAR1-dependent calcium flux assay was employed to screen for functional hPAR1 antagonist antibodies. Thrombin is known to cleave the N-terminal domain of PAR1, removing approximately 15 amino acids. The remaining N-terminal domain, referred to as the tethered ligand, is responsible for the initiation of PAR1 mediated signaling. This cleavage of PAR-1 by thrombin results in a rapid and transient calcium flux in cells can be measured using commercially available reagents (Molecular Devices). Specifically, purified antibodies were evaluated on HT-29, HCT-116 and DU145 cells for their ability to inhibit calcium flux after thrombin treatment. Cells in FlipR dye (Molecular Devices, Sunnyvale, Calif.) were pre-incubated with protein G purified antibodies for 1 hour, and Ca2+ flux was induced with thrombin at various concentrations. The results indicate that a subclone from each of two clones (4E7.J14 & 6E11.H6) showed strong antagonist activity. The FlipR assay was also run on the functional clones using both DU145 and HCT116 cells. Both cell lines confirmed the activity of the functional antibody antagonists.

In order to evaluate the mechanism of the antagonists, the antibodies were also examined for their ability to bind to the PAR1 receptor after cleavage by thrombin. The PAR1/thioredoxin was cleaved to completion with thrombin. After neutralizing the thrombin, an equal portion of full length PAR1/thioredoxin protein was added. Antibodies were bound to Protein G, and the immobilized antibodies were used to immunoprecipitate the cleaved/full length PAR1 fusion protein mixture. The resin was isolated, washed, and the captured proteins identified by SDS-PAGE. Three of the clones evaluated were able to bind to the portion of PAR1 adjacent to the thioredoxin fusion protein, including the two functional clones 4E7 and 6E11. This domain of PAR1 is representative of the tethered ligand that remains on the cell surface after thrombin cleavage. The results also indicate that antibodies that blocked thrombin cleavage of PAR1 but failed to bind to the tethered ligand were much less potent in FlipR assays. Thus, it appears that binding to the tethered ligand is necessary, though not sufficient for functional activity.

Regions of the two functional antibody heavy chain (VH) and light chain (VL) were cloned out by RT-PCR. Sequences of the primers used for identification of variable regions of the heavy and light chains for both clones (4E7.J14.L16 & 6E11.H6.A9) were the same, and are as follows. Primers for VH are: (1) HV1: GGGTCTAGACACCATGGRATG-SAGCTGKGTMATSCTCTT (SEQ ID NO:33) and (2) H-Constant: GCGTCTAGAAYCTCCACACACAGGRRC-CAGTGGATAGAC (SEQ ID NO:34). Primers for VL are: (1) LV5: GGGTCTAGACACCATGAAGTTGCCTGT-TAGGCTGTTGDNA (SEQ ID NO:35) and (2) L-Constant: GCGTCTAGAACTGGATGGTGGGAAGATGG (SEQ ID NO:36).

In brief, total RNA was isolated. RT-PCR was carried out with forward primers against signal sequence of either heavy or light chain variable regions, and reverse primers against heavy chain CH1 region or light chain kappa constant region. PCR products were cloned into pCR II or pcDNA3.1/V5-His-TPOP-TA vector for sequencing. Polynucleotide sequences of the heavy chain and light chain variable region sequences of these antibody clones were then determined (FIG. 1). The corresponding amino acid sequences of the variable regions are shown in FIG. 2. Also indicated in FIG. 2 are the CDR regions and the framework regions deduced in accordance with the numbering system of Kabat et al., supra.

Example 2

Generation of Chimeric Anti-hPAR1 Antibodies

This Example describes the generation and characterization of chimeric anti-hPAR1 antibodies. The chimeric antibodies contain variable regions from the above noted mouse anti-hPAR1 antibody and constant regions from human immunoglobulins.

To generation the chimeric antibodies, the variable regions of the mouse antibody against the human PAR1 clone were re-PCRed with primers designed for cloning into cassette vectors. They were then respectively cloned into cassette vectors which contain in-frame fusions with human immunoglobulin leader sequences, J-segments and splicer-donor signals. The sequences were then transferred into mammalian expression vectors containing human immunoglobulin constant region, neomycin selection on heavy chain, dhfr selection on light chain, and gene amplification using methotrexate.

DNA plasmids of chimeric IgG1 heavy chain and kappa light chain were co-electroporated into SP2/0 myeloma cells. The cells were selected with geneticin, and then cultured and expanded in growth medium containing geneticin and methotrexate. Cells were adapted into serum-free medium for antibody purification. Chimeric IgG1 antibodies secreted from transfected SP2/0 cells were purified. Antagonist activity of the purified chimeric IgG1 antibodies can be similarly examined in the FlipR assay as the mouse anti-hPAR1 antibodies. The test could reveal that the chimeric anti-hPAR1 antibodies exhibit similar antagonist activity as that of the mouse IgG1 antibody.

Example 3

Anti-hPAR1 Antibody Inhibits Thrombin Mediated IL-8 Secretion

This Example describes inhibition of thrombin-mediated IL-8 secretion from HUVECs by the anti-hPAR1 antagonist antibodies. Cells were exposed to thrombin overnight which resulted in the elevation of IL-8 secreted into the media. Antibodies were added 1 hour prior to thrombin treatment. The results as measured by ELISA are shown in FIG. 3. As demonstrated in the figure, the two mouse anti-hPAR1 antibodies were all able to inhibit the increase in IL-8 secretion from HUVECs that were treated with thrombin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An antibody or antigen binding molecule that specifically binds to an epitope of human PAR1 which antibody or antigen binding molecule comprises heavy chain complementarity determining region (CDR) sequences CDR1, CDR2, and CDR3 of SEQ ID NO:21, SEQ ID NO:22 and SEQ ID NO:23, respectively; and light chain CDR sequences CDR1, CDR2, and CDR3 of SEQ ID NO:24, SEQ ID NO:25, and SEQ ID NO:26, respectively, and wherein the antibody or antigen binding molecule is a PAR1 antagonist.

2. An antibody or antigen binding molecule that specifically binds to an epitope of human PAR1, which antibody or antigen binding molecule comprises a heavy chain complementarity determining region (CDR) sequences CDR1, CDR2, and CDR3 of SEQ ID NO:27, SEQ ID NO:28 and SEQ ID NO:29, respectively; and light chain CDR sequences CDR1, CDR2, and CDR3 of SEQ ID NO:30, SEQ ID NO:31, and SEQ ID NO:32, respectively, and wherein the antibody or antigen binding molecule is a PAR1 antagonist.

3. The antibody or antigen-binding molecule of claim 1 which comprises a heavy chain variable region amino acid sequence of SEQ ID NO:5 and a light chain variable region amino acid sequence of SEQ ID NO:6.

4. The antibody or antigen-binding molecule of claim 1 which is a mouse antibody.

5. The antibody or antigen-binding molecule of claim 1 which is a monoclonal antibody.

6. The antibody or antigen-binding molecule of claim 1 which is a chimeric antibody.

7. The antibody or antigen-binding molecule of claim 6 which comprises a human heavy chain constant region and a human light chain constant region.

8. The antibody or antigen-binding molecule of claim 1 which is a humanized antibody.

9. The antibody or antigen-binding molecule of claim 1 which is a single chain antibody.

10. The antibody or antigen-binding molecule of claim 1 which is a Fab fragment.

11. The antibody or antigen-binding molecule of claim 1 which is a monobody with a scaffold derived from a human fibronectin type III domain.

12. A pharmaceutical composition comprising an antibody or antigen binding molecule that specifically binds to an epitope of human PAR1, wherein the antibody or antigen binding molecule comprises heavy chain CDR1, CDR2, and CDR3 sequences, SEQ ID NO:21, SEQ ID NO:22 and SEQ ID NO:23, respectively; and light chain CDR1, CDR2, and CDR3 sequences, SEQ ID NO:24, SEQ ID NO:25, and SEQ ID NO:26, respectively, and wherein the antibody or antigen binding molecule is a PAR1 antagonist.

13. A pharmaceutical composition comprising an antibody or antigen binding molecule that specifically binds to an epitope of human PAR1, wherein the antibody or antigen binding molecule comprises heavy chain CDR1, CDR2, and CDR3 sequences, SEQ ID NO:27, SEQ ID NO:28 and SEQ ID NO:29, respectively; and light chain CDR1, CDR2, and CDR3 sequences, SEQ ID NO:30, SEQ ID NO:31, and SEQ ID NO:32, respectively, and wherein the antibody or antigen binding molecule is a PAR1 antagonist.

14. The antibody or antigen-binding molecule of claim 2 which comprises a heavy chain variable region amino acid sequence of SEQ ID NO:7 and a light chain variable region amino acid sequence of SEQ ID NO:8.

15. The antibody or antigen-binding molecule of claim 2 which is a mouse antibody.

16. The antibody or antigen-binding molecule of claim 2 which is a monoclonal antibody.

17. The antibody or antigen-binding molecule of claim 2 which is a chimeric antibody.

18. The antibody or antigen-binding molecule of claim 17 which comprises a human heavy chain constant region and a human light chain constant region.

19. The antibody or antigen-binding molecule of claim 2 which is a humanized antibody.

20. The antibody or antigen-binding molecule of claim 2 which is a single chain antibody.

21. The antibody or antigen-binding molecule of claim 2 which is a Fab fragment.

22. The antibody or antigen-binding molecule of claim 2 which is a monobody with a scaffold derived from a human fibronectin type III domain.

* * * * *